US00RE36481E

United States Patent [19]

Inamine et al.

[11] E Patent Number: Re. 36,481

[45] Reissued Date of Patent: Jan. 4, 2000

[54] HMG-COA REDUCTASE INHIBITORS

[75] Inventors: Edward S. Inamine, Rahway; Otto D. Hensens, Red Bank, both of N.J.; David R. Houck, Los Alamos, N.Mex.; Ta J. Lee; Robert L. Smith, both of Lansdale, Pa.; Wasyl Halczenko, Hatfield, Pa.; George D. Hartman, Lansdale, Pa.; Gerald E. Stokker, Gwynedd Valley, Pa.

[73] Assignee: Merck & Co., Inc., Rahway, N.J.

[21] Appl. No.: 09/188,158

[22] Filed: Nov. 4, 1998

Related U.S. Patent Documents

Reissue of:

[64] Patent No.: 4,940,727
Issued: Jul. 10, 1990
Appl. No.: 07/254,525
Filed: Oct. 6, 1988

U.S. Applications:

[63] Continuation-in-part of application No. 07/092,393, Sep. 2, 1987, abandoned, and application No. 07/048,136, May 15, 1987, abandoned, which is a continuation-in-part of application No. 07/001,933, Oct. 9, 1987, abandoned, which is a continuation-in-part of application No. 06/877,041, Jun. 23, 1986, abandoned.

[51] Int. Cl.[7] ..... A61K 31/335; C07D 315/00

[52] U.S. Cl. ..... 514/450; 514/460; 549/292

[58] Field of Search ..... 549/292; 514/450, 514/460

[56] References Cited

U.S. PATENT DOCUMENTS

| | | | |
|---|---|---|---|
| 4,231,938 | 11/1980 | Monaghan et al. | 260/343.5 |
| 4,294,846 | 10/1981 | Albers-Schonberg et al. | 424/279 |
| 4,351,844 | 9/1982 | Patchett et al. | 424/279 |
| 4,361,515 | 11/1982 | Terahara et al. | 549/292 |
| 4,376,863 | 3/1983 | Lam | 549/292 |
| 4,444,784 | 4/1984 | Hoffman et al. | 424/279 |
| 4,448,979 | 5/1984 | Terahara et al. | 549/292 |
| 4,450,171 | 5/1984 | Hoffman et al. | 514/460 |
| 4,517,373 | 5/1985 | Terahara et al. | 549/292 |
| 4,537,859 | 8/1985 | Terahara et al. | 435/146 |
| 4,661,483 | 4/1987 | Hoffman et al. | 514/316 |
| 4,668,699 | 5/1987 | Hoffman et al. | 514/824 |
| 4,766,145 | 8/1988 | Lee et al. | 514/460 |
| 4,795,811 | 1/1989 | Graham et al. | 544/6 |
| 4,831,165 | 5/1989 | Schuda et al. | 549/214 |
| 4,841,074 | 6/1989 | Lee et al. | 549/292 |
| 4,847,306 | 7/1989 | Lee et al. | 514/824 |
| 4,855,456 | 8/1989 | Lee et al. | 549/214 |
| 4,857,546 | 8/1989 | Duggan et al. | 514/460 |
| 4,857,547 | 8/1989 | Hoffman et al. | 514/460 |
| 4,876,364 | 10/1989 | Schuda et al. | 549/214 |
| 4,894,465 | 1/1990 | Lee et al. | 549/214 |
| 4,894,466 | 1/1990 | Lee et al. | 549/292 |
| 4,916,162 | 4/1990 | Hoffman et al. | 514/574 |
| 4,937,263 | 6/1990 | Hoffman et al. | 514/510 |
| 4,946,864 | 8/1990 | Prugh et al. | 514/460 |
| 4,997,755 | 3/1991 | Williamson et al. | 435/125 |

FOREIGN PATENT DOCUMENTS 59 122 483 12/1982 Japan .

OTHER PUBLICATIONS

G. E. Stokker et al., "3–Hydroxy–3–methylglutarylcoenzyme A Reductase Inhibitors. 1. Structural Modification of 5–Substituted 3,5, Dihydroxypentanoic Acids and Their Lactone Derivatives", J. Med. Chem., 28, pp. 347–358 (1985).

R. A. Heller et al., "3–Hydroxy–3–methylglutaryl Coenzyme A Reductase from Rat Liver", J. Biol. Chem., 251, pp. 3815–3822 (1976).

D. A. Kleinsek et al., "Purification of 3–hydroxy–3–methylglutaryl–coenzyme A reducatase from rat liver", Proc. Nat'l Acad. Sci. USA, 74, pp. 1431–1435 (1977).

S. Shefer et al., "HMG CoA reductase of intestinal mucosa and liver of the rat", J. Lipid Res., 13, pp. 402–412 (1972).

Sugiyama et al., Chemical Abstracts, 111, Abstract No. 120925n, pp. 366–367 (1989).

A. F. Rosenthal et al., "Compounds Related to a–Glycerophosphoric Acid, Phosphorylcholine and Phosphorylethanolamine", J. Amer. Chem. Soc., 80, pp. 5240–5241 (1959).

A. G. Olsson et al., "Synvinolin In Hypercholesterolaemia", The Lancet, pp. 390–391 Aug. 16, 1986.

(List continued on next page.)

*Primary Examiner*—Amelia Owens
*Attorney, Agent, or Firm*—Carol S. Quagliato; Melvin Winokur

[57] ABSTRACT

Novel 3-hydroxy-3-methylglutaryl-coenzyme A (HMG-CoA) reductase inhibitors are useful as antihypercholesterolemic agents and are represented by the following general structural formulae (I) and (II):

(I)

(II)

29 Claims, No Drawings

OTHER PUBLICATIONS

P. Weisweiler et al., "Colestipol Plus Fenofibrate Versus Synvinolin In Familial Hypercholesterolaemia", The Lancet, pp. 1212–1213, Nov. 22, 1986.

A. F. Stalenhoef et al., "Effect of Synvinolin, a New Cholesterol Synthesis Inhibitor, in Familial Hypercholesterolemia", Arteriosclerosis, vol. 6, No. 5, Sep./Oct. 1986.

M.J.T.M. Mol et al., "Effects of Synvinolin (MK–733) On Plasma Lipids In Familial Hypercholesterolaemia", The Lancet, pp. 936–939, Oct. 25, 1986.

S. M. Grundy et al., "Effects of Mevinolin on Plasma Lipoprotein (LP) Metabolism in Moderate Hypercholesterolemia", ABSTRACTS Circulation, vol. 70, Supp. II, p. 268, No. 1072 (1984).

D. W. Bilheimer et al., "Mevinolin and colestipol stimulate receptor–mediated clearance of low density lipoprotein from plasma in familial hypercholesterolemia heterozygotes", Proc. Natl. Acad. Sci. USA, vol. 80, pp. 4124–4128 (Jul. 1983).

D. W. Bilheimer et al., "Mevinolin Stimulates Receptor–Mediated Clearance of LDL in Familial Hypercholesterolemia (FH) Heterozygotes", Clin. Res. 31, No. 2, p. 544A (1983).

J. A. Tobert et al., Cholesterol–lowering effect of Mevinolin, an Inhibitor of 3–Hydroxy–3–Methylglutaryl–Coenzyme A Reductase, in Healthy Volunteers, J. Clin. Invest. (USA), 69(4), PP. 913–919 (Apr. 1982).

J. A. Tobert et al., "Rapid and Substantial Lowering of Human Serum Cholesterol by Mevinolin (MK–803), An Inhibitor of Hydroxymethylglutaryl–Coenzyme A Reductase", Atherosclerosis, 41, pp. 61–65 (1982).

HMG-COA REDUCTASE INHIBITORS

Matter enclosed in heavy brackets [ ] appears in the original patent but forms no part of this reissue specification; matter printed in italics indicates the additions made by reissue.

This Application is a continuation-in-part of U.S. patent application Ser. No. 092,353, filed Sept. 2, 1987 and U.S. patent application Ser. No. 048,136 filed May 15, 1987, which is a continuation-in-part of Ser. No. 001,933 filed Oct. 9, 1987, which is a continuation-in-part of Ser. No. 877,041 filed June 23, 1986, all now abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that functions by limiting cholesterol biosynthesis by inhibiting the enzyme HMG-CoA reductase. In addition to the natural fermentation products, mevastatin and lovastatin, there are a variety of semi-synthetic and totally synthetic analogs thereof.

The naturally occurring compounds and their semisynthetic analogs have the following general structural formulae:

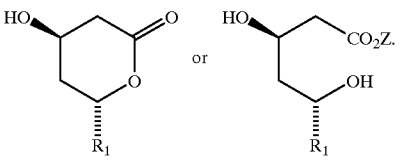

wherein:

Z is hydrogen, $C_{1-5}$ alkyl or $C_{1-5}$ alkyl substituted with a member of the group consisting of phenyl, dimethylamino, or acetylamino; and $R_1$ is:

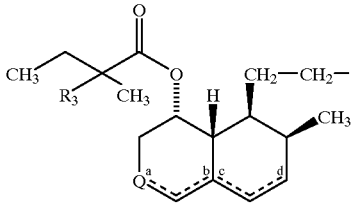

wherein Q is

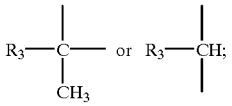

$R_3$ is H or OH; and $R_2$ is hydrogen or methyl; and a, b, c, and d represent optional double bonds, especially where b and d represent double bonds or a, b, c, and d are all single bonds.

U.S. Pat. No. 4,517,373 discloses semisynthetic hydroxy containing compounds represented by the above general formula wherein $R_1$ is

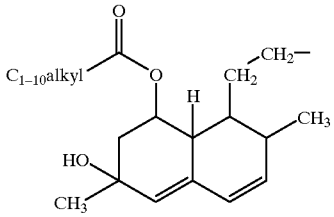

and

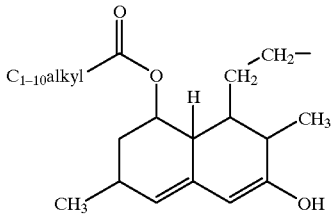

U.S. Pat. No. 4,517,859 and U.S. Pat. No. 4,448,979 also disclose semisynthetic hydroxy-containing compounds represented by the above general formula wherein $R_1$ is

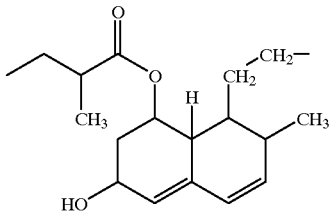

and

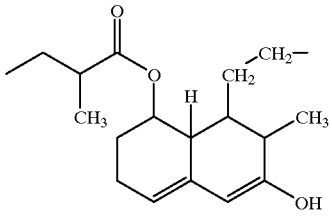

These compounds are prepared by the action of certain microorganisms on the corresponding non-hydroxylated substrates. One such organism described in U.S. Pat. No. 4,537,859 is of the genus Nocardia.

U.S. Pat. No. 4,376,863 discloses a fermentation product, isolated after cultivation of a microorganism belonging to the genus Aspergillus, which has a hydroxy-containing butyryloxy side chain and is represented by the above general formula wherein $R_1$ is

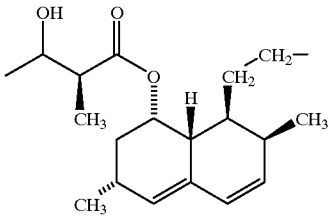

Japanese unexamined patent application No. J59-122,483-A discloses a semisynthetic hydroxy-containing compound represented by the above general formula wherein $R_1$ is

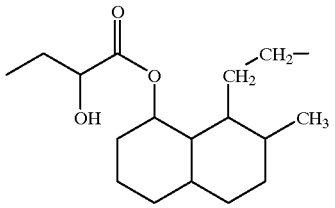

SUMMARY OF THE INVENTION

This invention relates to novel compounds which are HMG-CoA reductase inhibitors and are useful as antihypercholesterolemic agents. Specifically, the compounds of this invention are analogs of mevinolin and related compounds which possess a hydroxyalkyl group, acyloxyalkyl or carbamoyloxyalkyl group of the structure

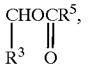

a carboxy group, an alkoxycarbonyl group, a carbamoyl group of structure

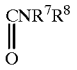

or a ketone group of the structure

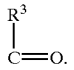

substituted on the 6-position of the polyhydronaphthyl moiety. Additionally, pharmaceutical compositions of these novel compounds, as the sole therapeutically active ingredient and in combination with bile acid sequestrants, are disclosed. Other embodiments of this invention are methods of treating disease conditions in which hypercholesterolemia is an etiological factor, and processes for preparing the novel compounds.

DETAILED DESCRIPTION OF THE INVENTION

The specific HMG-CoA reductase inhibitors of this invention are the compounds represented by the following general structural formulae (I) and (II):

(I)

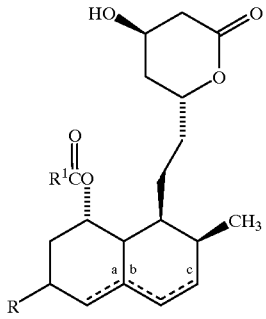

(II)

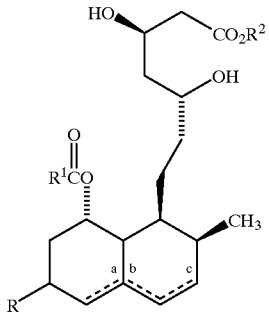

wherein:

R is

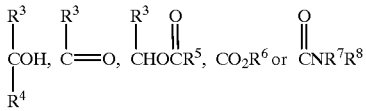

$R^1$ and $R^5$ are independently:

(1) $C_{1-10}$ alkyl;

(2) substituted $C_{1-10}$ alkyl in which one or more substituent(s) is:

(a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, (h) substituted phenyl in which the substituents are X and Y, (i) $C_{1-10}$ alkyl$S(O)_n$ in which n is 0 to 2, (j) $C_{3-8}$ cycloalkyl$S(O)_n$, (k) phenyl$S(O)_n$, (l) substituted phenyl$S(O)_n$ in which the substituents are X and Y, and (m) oxo;

(3) $C_{1-10}$ alkoxy;

(4) $C_{2-10}$ alkenyl;

(5) $C_{3-8}$ cycloalkyl;

(6) substituted $C_{3-8}$ cycloalkyl in which one substituent is:

(a) $C_{1-10}$ alkyl, (b) substituted $C_{1-10}$ alkyl in which the substituent is:

(i) halogen, (ii) hydroxy, (iii) $C_{1-10}$ alkoxy, (iv) $C_{1-5}$ alkoxycarbonyl, (v) $C_{1-5}$ acyloxy,
(vi) phenyl,
(vii) substituted phenyl in which the substituents are X and Y,
(viii) $C_{1-10}$ alkylS(O)$_n$.
(ix) $C_{3-8}$ cycloalkylS-(O)$_n$
(x) phenylS(O)$_n$,
(xi) substituted phenylS(O)$_n$ in which the substituents are X and Y, and
(xii) oxo,
(c) $C_{1-10}$ alkylS(O)$_n$,
(d) $C_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;

(7) phenyl;

(8) substituted phenyl in which the substituents are X and Y;

(9) amino;

(10) $C_{1-5}$ alkylamino;

(11) di($C_{1-5}$ alkyl)amino;

(12) phenylamino;

(13) substituted phenylamino in which the substituents are X and Y;

(14) phenyl $C_{1-10}$ alkylamino;

(15) substituted phenyl $C_{1-10}$ alkylamino in which the substituents are X and Y;

(16) a member selected from:
(a) piperidinyl,
(b) pyrrolidinyl,
(c) piperazinyl,
(d) morpholinyl, and
(e) thiomorpholinyl; and

(17) $R^9$S in which $R^9$ is:
(a) $C_{1-10}$ alkyl,
(b) phenyl, and
(c) substituted phenyl in which the substituents are X and Y;

$R^2$ and $R^6$ are independently (1) hydrogen;

(2) $C_{1-5}$ alkyl;

(3) substituted $C_{1-5}$ alkyl in which the substituent is
(a) phenyl,
(b) dimethylamino, and
(c) acetylamino, and (4) 2,3-dihydroxypropyl;

$R^3$ and $R^4$ are independently:

(1) hydrogen;

(2) $C_{1-10}$ alkyl;

(3) substituted $C_{1-10}$ alkyl in which one or more substituent(s) is
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkylS(O)$_n$,
(j) $C_{3-8}$ cycloalkylS(O)$_n$,
(k) phenylS(O)$_n$,
(l) substituted phenylS(O)$_n$ in which the substituents are X and Y, and
(m) oxo;

(4) $C_{2-10}$ alkenyl;

(5) substituted $C_{2-10}$ alkenyl in which one or more substituent(s) is:
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkylS(O)$_n$,
(j) $C_{3-8}$ cycloalkylS(O)$_n$,
(k) phenylS(O)$_n$,
(l) substituted phenylS(O)$_n$ in which the substituents are X and Y, and
(m) oxo;

(6) $C_{3-8}$ cycloalkyl;

(7) substituted $C_{3-8}$ cycloalkyl in which one substituent is:
(a) $C_{1-10}$ alkyl,
(b) substituted $C_{1-10}$ alkyl in which the substituent is:
(i) halogen,
(ii) hydroxy,
(iii) $C_{1-10}$ alkoxy,
(iv) $C_{1-5}$ alkoxycarbonyl,
(v) $C_{1-5}$ acyloxy
(vi) phenyl,
(vii) substituted phenyl in which the substituents are X and Y,
(viii) $C_{1-10}$ alkylS(O)$_n$,
(ix) $C_{3-8}$ cycloalkylS(O)$_n$,
(x) phenylS(O)$_n$,
(xi) substituted phenylS(O)$_n$ in which the substituents are X and Y, and
(xii) oxo,
(c) $C_{1-10}$ alkylS(O)$_n$,
(d) $C_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;

(8) phenyl;

(9) substituted phenyl in which the substituents are X and Y;

$R^7$ and $R^8$ are independently:

(1) hydrogen;

(2) $C_{1-10}$ alkyl;

(3) substituted $C_{1-10}$ alkyl in which one or more substituent(s) is (a) halogen,
(b) hydroxy,
(c) $C_{1-10}$ alkoxy,
(d) $C_{1-10}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkyl $S(O)_n$ in which n is 0 to 2,
(j) $C_{3-8}$ cycloalkyl $S(O)_n$,
(k) phenyl $S(O)_n$;
(l) substituted phenyl $S(O)_n$ in which the substituents are X and Y, and
(m) oxo;

(4) $C_{2-10}$ alkenyl;

(5) $C_{3-8}$ cycloalkyl;

(6) aminocarbonyl;

(7) substituted aminocarbonyl in which one or more substituent(s) is
(a) $C_{1-5}$ alkyl,
(b) $C_{3-8}$ cycloalkyl,
(c) phenyl,
(d) substituted phenyl in which the substituents are X and Y;

(8) phenyl;

(9) substituted phenyl in which the substituents are X and Y;

(10) $C_{1-10}$ alkylcarbonyl;

(11) $C_{3-8}$ cycloalkylcarbonyl;

(12) phenylcarbonyl;

(13) substituted phenylcarbonyl in which the substituents are X and Y; and

(14) a nitrogen-containing heterocyclic group selected from piperidinyl, pyrrolidinyl, piperazinyl, morpholinyl and thiomorpholinyl; and X and Y independently are hydrogen, halogen, trifluoromethyl, $C_{1-3}$ alkyl, nitro, cyano or a group selected from:

(1) $R^{10}O(CH_2)_m$ in which m is 0 to 3 and $R^{10}$ is hydrogen, $C_{1-3}$alkyl or hydroxy-$C_{2-3}$alkyl;

(2)

$$R^{11}\overset{\overset{\displaystyle O}{\|}}{C}O(CH_2)_m \quad \text{or} \quad R^{11}O\overset{\overset{\displaystyle O}{\|}}{C}O(CH_2)_m$$

in which $R^{11}$ is hydrogen, $C_{1-3}$alkyl, hydroxy-$C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy-$C_{2-3}$alkylamino-$C_{1-3}$alkyl or di(hydroxy-$C_{2-3}$alkyl) amino-$C_{1-3}$alkyl;

(3)

$$R^{12}O\overset{\overset{\displaystyle O}{\|}}{C}(CH_2)_m$$

in which $R^{12}$ is hydrogen, $C_{1-3}$alkyl, hydroxy-$C_{2-3}$ alkyl, $C_{1-3}$alkoxy-$C_{1-3}$alkyl, phenyl or naphthyl;

(4)

$$R^{13}R^{14}N(CH_2)_m, \quad R^{13}R^{14}N\overset{\overset{\displaystyle O}{\|}}{C}(CH_2)_m \quad \text{or} \quad R^{13}R^{14}N\overset{\overset{\displaystyle O}{\|}}{C}O(CH_2)_m$$

in which $R^{13}$ and $R^{14}$ independently are hydrogen, $C_{1-3}$ alkyl, hydroxy-$C_{2-3}$alkyl or together with the nitrogen atom to which they are attached form a heterocyclic group selected from piperidinyl, pyrrolidinyl, piperazinyl, morpholinyl or thiomorpholinyl;

(5) $R^{15}S(O)_n(CH_2)_m$ in which $R^{15}$ is hydrogen, $C_{1-3}$alkyl, amino, $C_{1-3}$alkylamino or di($C_{1-3}$alkyl)amino; and a, b and c each represent single bonds or one of a, b and c represents a double bond or both a and c represent double bonds;

or a pharmaceutically acceptable salt thereof.

Except where specifically defined to the contrary, the terms "alkyl", "alkoxy" and "acyl" include both the straight-chain and branched-chain species of the term.

One embodiment of this invention is the class of compounds of the formulae (I) and (II) wherein:

$R^1$ and $R^5$ are independently selected from:

(1) $C_{1-10}$ alkyl;

(2) substituted $C_{1-10}$ alkyl in which one or more substituent(s) is:
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y, and
(i) oxo;

(3) $C_{3-8}$ cycloalkyl;

(4) substituted $C_{3-8}$ cycloalkyl in which one substituent is:
(a) $C_{1-10}$ alkyl,
(b) substituted $C_{1-10}$ alkyl in which the substituent is selected from
(i) halogen,
(ii) hydroxy,
(iii) $C_{1-10}$ alkoxy
(iv) $C_{1-5}$ acyloxy,
(v) $C_{1-5}$ alkoxycarbonyl,
(vi) phenyl,
(vii) subsituted phenyl in which the substituents are X and Y, and
(viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;

(5) phenylamino;

(6) substituted phenylamino in which the substituents are X and Y;

(7) phenyl$C_{1-10}$ alkylamino; and (8) substituted phenyl$C_{1-10}$ alkylamino in which the substituents are X and Y.

One subclass of this embodiment is the compounds of formulae (I) and (II) wherein:

$R^1$ and $R^5$ are independently:

(1) $C_{1-10}$ alkyl;

(2) $C_{3-8}$ cycloalkyl;

(3) phenylamino; and (4) substituted phenylamino in which the substituents are X and Y.

Illustrating this subclass are the compounds wherein $R^3$ and $R^4$ are independently:

(1) hydrogen (2) $C_{1-10}$ alkyl;

(3) $C_{3-8}$ cycloalkyl;

(4) phenyl.

Further illustrating this subclass are those compounds wherein $R^7$ and $R^8$ are independently:

(1) hydrogen, (2) $C_{1-10}$alkyl, (3) $C_{3-8}$cycloalkyl, (4) aminocarbonyl, (5) substituted amino carbonyl in which one or more substituents is (a) $C_{1-5}$alkyl, (b) $C_{3-8}$cycloalkyl, (c) phenyl, (d) substituted phenyl in which the substituents are X and Y.

More specifically illustrating this subclass are those compounds of formula (I) and (II) wherein $R^1$ is 1,1-dimethylpropyl or sec-butyl and $R^3$ and $R^4$ are independently:

(1) hydrogen, (2) $C_{1-5}$alkyl, (3) phenyl.

Exemplifying this subclass are those compounds of the formulae (I) and(II) wherein both a and c represent double bonds, especially the following compounds:

(1) 6(R)-[2-[8(S)-(2,2-dimethylbutyryloxy)-2(S)-methyl6(S)-(hydroxymethyl)-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-(2,2-dimethylbutyryl-oxy)-2(S)-methyl-6(R)-(hydroxymethyl)-1,2,6,7,8,8a(R)-hexahydronaphthyl-1(S)]ethyl]-4(R)-hydroxy-3,4,5,6-tetrahydro-2H-pyran-2-one;

(3) 6(R)-[2-[8(S)-(2-methylbutyryloxy)-2(S)-methyl-6(S)-(hydroxymethyl)-1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-(2-methylbutyryloxy)-2(S)-methyl-6(R)-(hydroxymethyl)-1,2,6,7,8,8a(R)-hexahydronaphthyl-1(S)]ethyl]-4(R)-hydroxy-3,4,5,6-tetrahydro-2H-pyran-2-one; and (5) 6(R)-[2-[8(S)-(2,2-dimethylbutyryloxy)-2(S)-methyl-6(S)-carboxy-1,2,6,7,8,8a(R)-hexahydronaphthyl-1(S)]ethyl]-4(R)-hydroxy-3,4,5,6-tetrahydro-2H-pyran-2-one;

(6) 6(R)-[2-[8(S)-(2-methylbutyryloxy)-2(S)-methyl-6(S)-carboxy-1,2,6,7,8,8a(R)-hexahydronaphthyl-1(S)]ethyl]-4(R)-hydroxy-3,4,5,6-tetrahydro-2H-pyran-2-one;

(7) 6(R)-[2-[8(S)-(2,2-dimethylbutyryloxy)-2(S)-methyl-6(R)-carboxy-1,2,6,7,8,8a(R)-hexahydronaphthyl-1(S)]ethyl]-4(R)-hydroxy-3,4,5,6-tetrahydro-2H-pyran-2-one;

(8) 6(R)-[2-[8(S)-(2,2-dimethylbutyryloxy)-2(S)-methyl-6(S)-(N,N-dimethyl)aminocarbonyl-1,2,6,7,8,8a(R)-hexahydronaphthyl-1(S)]ethyl]-4(R)-hydroxy-3,4,5,6-tetrahydro-2H-pyran-2-one;

(9) 6(R)-[2-(8(S)-(2,2-dimethylbutyryloxy)-2(S)-methyl-6(R)-aminocarbonyl-1,2,6,7,8,8a(R)-hexahydronaphthyl-1(S)]ethyl]-4(R)-hydroxy-3,4,5,6-tetrahydro-2H-pyran-2-one;

(10) 6(R)-[2-(8(S)-(2-methylbutyryloxy)-2(S)-methyl-6(S)-aminocarbonyl-1,2,6,7,8,8a(R)-hexahydronaphthyl-1(S)]ethyl]-4(R)-hydroxy-3,4,5,6-tetrahydro-2H-pyran-2-one; and the corresponding dihydroxy acids, and esters thereof.

Another exemplification of the subclass wherein a and c are both double bonds are the following compounds.

(1) 6(R)-[2-[8(S)-(2,2-dimethylbutyryloxy)-2(S)-methyl-6(S)-(1-hydroxyethyl)-1,2,6,7,8,8a-(R)-hexahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-(1-hydroxyethyl)-1,2,6,7,8,8a(R)-hexahydronaphthyl-1(S)]ethyl]-4(R)-hydroxy-3,4,5,6-tetrahydro-2H-pyran-2-one;

(3) 6(R)-[2-[8(S)-(2-methylbutyryloxy)-2(S)-methyl-6(S)-(1-hydroxyethyl)-1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-(2-methylbutyryloxy)-2(S)-methyl-6(R)-(1-hydroxyethyl)-1,2,6,7,8,8a(R)-hexahydronaphthyl-1(S)]ethyl]-4(R)-hydroxy-3,4,5,6-tetrahydro-2H-pyran-2-one; and the corresponding ring opened dihydroxy acids, and esters thereof.

Another example of this subclass are those compounds of the formulae (I) and (II) wherein a, b and c represent single bonds, especially the following compounds:

(1) 6(R)-[2-[8(S)-(2,2-dimethylbutyryloxy)-2(S)-methyl-6(S)-hydroxymethyl-1,2,3,4,4a(S),5,6,7,8,8a(S)-decahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(S)-(2,2-dimethylbutyryloxymethyl)-1,2,3,4,4a(S),5,6,7,8,8a(S)-decahydronaphthyl-1(S)]ethyl]-4(R) -hydroxy-3,4,5,6-tetrahydro-2H-pyran-2-one;

(3) 6(R)-[2-[8(S)-(2,2-dimethylbutyryloxy)-2(S)-methyl-6(S)-carboxy-1,2,3,4,4a(S),5,6,7,8,8a(S)-decahydronaphthyl-1(S)]ethyl]-4(R)-hydroxy-3,4,5,6-tetrahydro-2H-pyran-2-one;

(4) 6(R)-[2-[8(S)-(2,2-dimethylbutyryloxy)-2(S)-methyl-6(S)-ethoxycarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one;

(5) 6(R)-[2-[8(S)-(2,2-dimethylbutyryloxy)-2(S)-methyl-6(S)-aminocarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one;

(6) 6(R)-[2-[8(S)-(2,2-dimethylbutyryloxy)-2(S)-methyl-6(S)-(N-cyclohexylaminocarbonyl,N-cyclohexyl)aminocarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one;

(7) 6(R)-[2-[8(S)-(2,2-dimethylbutyryloxy)-2(S)-methyl-6(R)-(1-hydroxyethyl)-1,2,3,4,4a(S),5,6,7,8,8a(S)-decahydronaphthyl-1(S)]ethyl]-4(R)-hydroxy-3,4,5,6-tetrahydro-2H-pyran-2-one;

(8) 6(R)-[2-[8(S)-(2,2-dimethylbutyryloxy)-2(S)-methyl-6(S)-(1-hydroxyethyl)-1,2,3,4,4a(S),5,6,7,8,8a(S)-decahydronaphthyl-1(S)]ethyl]-4(R)-hydroxy-3,4,5,6-tetrahydro-2H-pyran-2-one;

(9) 6(R)-[2-(8(S)-(2,2-dimethylbutyryloxy)-2(S)-methyl-6(S)-(1-hydroxyphenylmethyl)-1,2,3,4,4a(S),5,6,7,8,8a(S)-decahydronaphthyl-1(S)]ethyl]-4(R)-hydroxy-3,4,5,6-tetrahydro-2H-pyran-2-one;

(10) 6(R)-[2-(8(S)-(2,2-dimethylbutyryloxy)-2(S)-methyl-6(S)-(1-oxoethyl)-1,2,3,4,4a(S),5,6,7,8,8a(S)-decahydronaphthyl-1(S)]ethyl]-4(R)-hydroxy-3,4,5,6-tetrahydro-2H-pyran-2-one and the corresponding ring opened dihydroxy acids, and esters thereof.

Another example of this subclass are those compounds of the formulae (I) and (II) wherein one of a, b or c represents a double bond, especially the following compounds:

(1) 6(R)-[2-[8(S)-(2,2-dimethylbutyryl-oxy)-2(S)-methyl-6(R)-hydroxymethyl-1,2,3,4,6,7,8,8a(R)-octahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-(2,2-dimethylbutyryloxymethyl)-1,2,3,4,6,7,8,8a(R)-octahydronaphthyl-(S)]ethyl]-4(R)-hydroxy-3,4,5,6-tetrahydro-2H-pyran-2-one;

(3) 6(R)-[2-[8(S)-(2,2-dimethylbutyryl-oxy)-2(S)-methyl-6(R)-(1-hydroxyethyl)-1,2,3,4,6,7,8,8a(R)-octahydronaphthyl-1(S)]ethyl]-4(R)-hydroxy-3,4,5,6-tetrahydro-2H-pyran-2-one; and the corresponding ring opened dihydroxy acids, and esters thereof.

The compounds of formulae (I) and (II) wherein a and c represent double bonds are conveniently prepared from lovastatin or its analogs having a 6-methyl group by one of the following three microbiological methods:

(a) adding the substrate to a growing culture of Nocardia autotrophica for a suitable incubation period followed by isolation, and derivatization if desired;

(b) collecting a culture of the bioconverting microorganism and contacting the collected cells with the substrate; or (c) preparing a cell-free, enzyme-containing extract from the cells of the bioconverting microorganism and contacting this extract with the substrate.

Cultivation of the bioconverting microorganism of the genus Nocardia can be carried out by conventional means in a conventional culture medium containing nutrients well known for use with such microorganisms. Thus, as is well known, such culture media contain sources of assimilable carbon and of assimilable nitrogen and often inorganic salts. Examples of sources of assimilable carbon include glucose, sucrose, starch, glycerin, millet jelly, molasses and soybean oil. Examples of sources of assimilable nitrogen include soybean solids (including soybean meal and soybean flour), wheat germ, meat extracts, peptone, corn steep liquor, dried yeast and ammonium salts, such as ammonium sulphate. If required, inorganic salts, such as sodium chloride, potassium chloride, calcium carbonate or phosphates, may also be included. Also, if desired, other additives capable of promoting the production of hydroxylation enzymes may be employed in appropriate combinations. The particular cultivation technique is not critical to the process of the invention and any techniques conventionally used for the cultivation of microorganisms may equally be employed with the present invention. In general, of course, the techniques employed will be chosen having regard to industrial efficiency. Thus, liquid culture is generally preferred and the deep culture method is most convenient from the industrial point of view.

Cultivation will normally be carried out under aerobic conditions and at a temperature within the range from 20° to 37° C., more preferably from 26° to 28° C.

Method (a) is carried out by adding the substrate to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the micro-organism begins to increase and this is usually 1 or 2 days after beginning cultivation of the microorganism. The amount of the substrate added is preferably from 0.01 to 5.0% by weight of the medium, more preferably from 0.05 to 0.5%, e.g., from 0.05 to 0.1% by weight. After addition of the substrate, cultivation is continued aerobically, normally at a temperature within the ranges proposed above. Cultivation is normally continued for a period of from 1 to 2 days after addition of the substrate.

In method (b), cultivation of the microorganism is first carried out under conditions such as to achieve its maximum hydroxylation capacity; this capacity usually reaches a maximum between 4 and 5 days after beginning the cultivation, although this period is variable, depending upon the nature and temperature of the medium, the species of microorganism and other factors. The hydroxylation capacity of the culture can be monitored by taking samples of the culture at suitable intervals, determining the hydroxylation capacity of the samples by contacting them with a substrate under standard conditions and determining the quantity of product obtained and plotting this capacity against time as a graph. When the hydroxylation capacity has reached its maximum point, cultivation is stopped and the microbial cells are collected. This may be achieved by subjecting the culture to centrifugal separation, filtration or similar known separation methods. The whole cells of the cultivating microorganism thus collected, preferably, are then washed with a suitable washing liquid, such as physiological saline or an appropriate buffer solution.

Contact of the collected cells of the microorganism of the genus Nocardia with the substrate is generally effected in an aqueous medium, for example in a phosphate buffer solution at a pH value of from 5 to 9. The reaction temperature is preferably within the range from 20° to 45° C., more preferably from 25° to 30° C. The concentration of the substrate in the reaction medium is preferably within the range from 0.01 to 5.0% by weight. The time allowed for the reaction is preferably from 1 to 5 days, although this may vary depending upon the concentration of the substrate in the reaction mixture, the reaction temperature, the hydroxylation capacity of the microorganism (which may, of course, vary from species to species and will also, as explained above, depend upon the cultivation time) and other factors.

The cell-free, enzyme-containing extract employed in method (c) may be obtained by breaking down the whole cells of the microorganism obtained as described in relation to method (b) by physical or chemical means, for example by grinding or ultrasonic treatment to provide a disintegrated cellular mass or by treatment with a surface active agent or an enzyme to produce a cellular solution. The resulting cell-free extract is then contacted with the substrate under the same conditions as are described above in relation to method (b).

The microorganism useful in the novel process of this invention is of the genus Nocardia. Of particular importance are the known strains of microorganism, Nocardia autotrophica, subspecies canberrica, ATCC 35203 of the culture MA-6181 and subspecies amethystina ATCC 35204 of the culture MA-6180 of the culture collection of Merck & Co., Inc., Rahway, N.J. It should be noted that the culture MA-6180 preferentially affords the hexahydronaphthyl compounds (a and c are double bonds) of this invention wherein R is $CH_2OH$, although the compounds wherein R is $CO_2H$ are also formed. Additionally, when the culture MA6181 is utilized in the bioconversion reaction, the compounds of the invention wherein R is $CO_2H$ are preferentially formed, although the compounds wherein R is $CH_2OH$ are also prepared. A sample of the culture designated ATCC 35203 and ATCC 35204 is available in the permanent culture collection of the American Type Culture Collection at 12301 Parklawn Drive, Rockville, Md. 20852.

A novel microorganism deposited in the culture collection of Merck & Co., Inc. and designated MA-6455 may also be utilized in the bioconversion reaction as described in copending patent application Ser. No. 181,877 filed Apr. 15, 1988.

After completion of the conversion reaction by any of the above methods, the desired compound can be directly isolated, separated or purified by conventional means. For example, separation and purification can be effected by filtering the reaction mixture, extracting the resulting filtrate with a water-immiscible organic solvent (such as ethyl acetate), distilling the solvent from the extract, subjecting the resulting crude compound to column chromatography, (for example on silica gel or alumina) and eluting the column with an appropriate eluent, especially in an HPLC apparatus.

The compound of formula (I) and (II) wherein a and c are double bonds may also be prepared following the synthetic methodology in copending patent applications Ser. No. 131,695 filed Feb. 24, 1988, and Ser. No. 161,530, Ser. No. 161,579, Ser. No. 161,529 all filed May 6, 1988. Lovastatin or a 8'-acyl analog is the the starting material in each case.

The compounds of formula (I) wherein a and c represent double bonds and R is $CO_2H$ can be converted cleanly, and without epimerization of the methine group to which R is appended, to the corresponding primary alcohols wherein R is $CH_2OH$ as illustrated in the following synthetic pathway:

but with cooling, preferably to −70° C., compound (2) is allowed to react with isobutyl chloroformate to afford the mixed anhydride (3). The resulting, cold solution of compound (3) is added to a cold, preferably 0° C., solution of a suitable reducing agent, such as sodium borohydride in a suitable organic solvent, such as ethanol, to afford compound (4). Alternatively compound (1) can be directly converted to compound (3) following the procedure in copending patent application Ser. No. 065,223 filed June 22, 1987.

Compounds of formula (I) wherein a and c are double bonds and R is $R^3CHOH$ are conveniently prepared from the aldehyde (i)

(i)

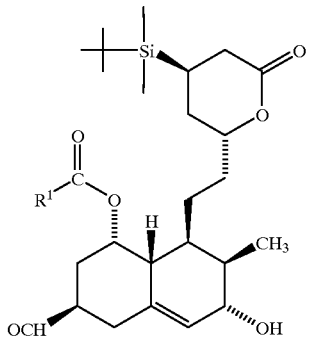

by the addition to the formyl group of a Grignard reagent or other alkylatinq agent followed by the removal of the 3'-OH group by the use of an acid such as HF. Aldehyde (i) is prepared as described in copending patent application Ser. No. 161529 filed Feb. 29, 1988.

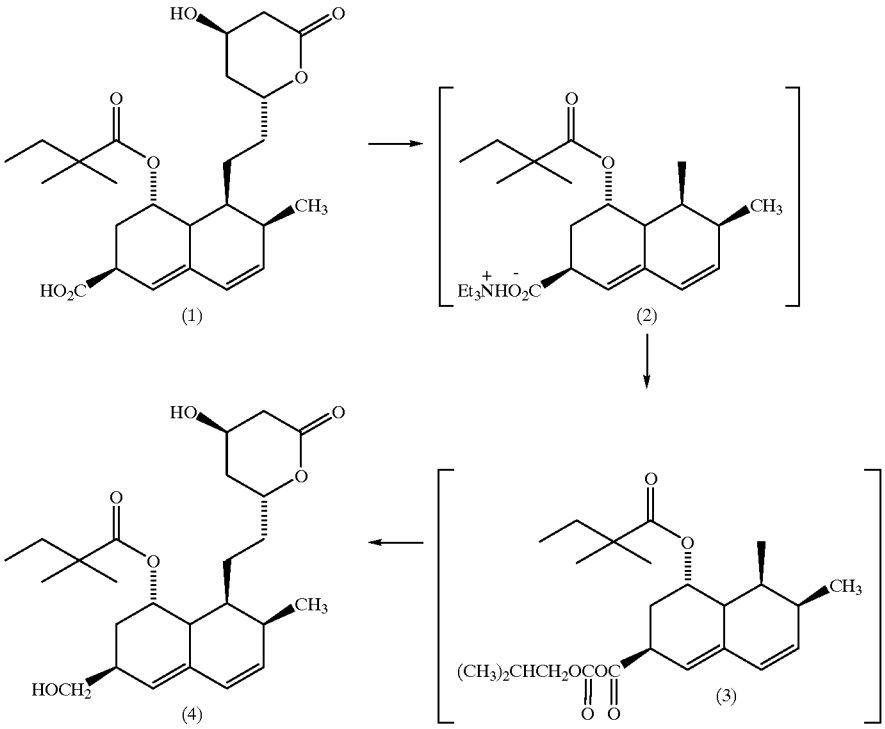

Compound (1) is converted to the corresponding triethylammonium salt (2) in a suitable organic solvent, preferably methylene chloride at room temperature. Without isolation The compounds of formulae (I) and (II) wherein a, b and c all represent single bonds are conveniently prepared from lovastatin via the following synthetic pathway:

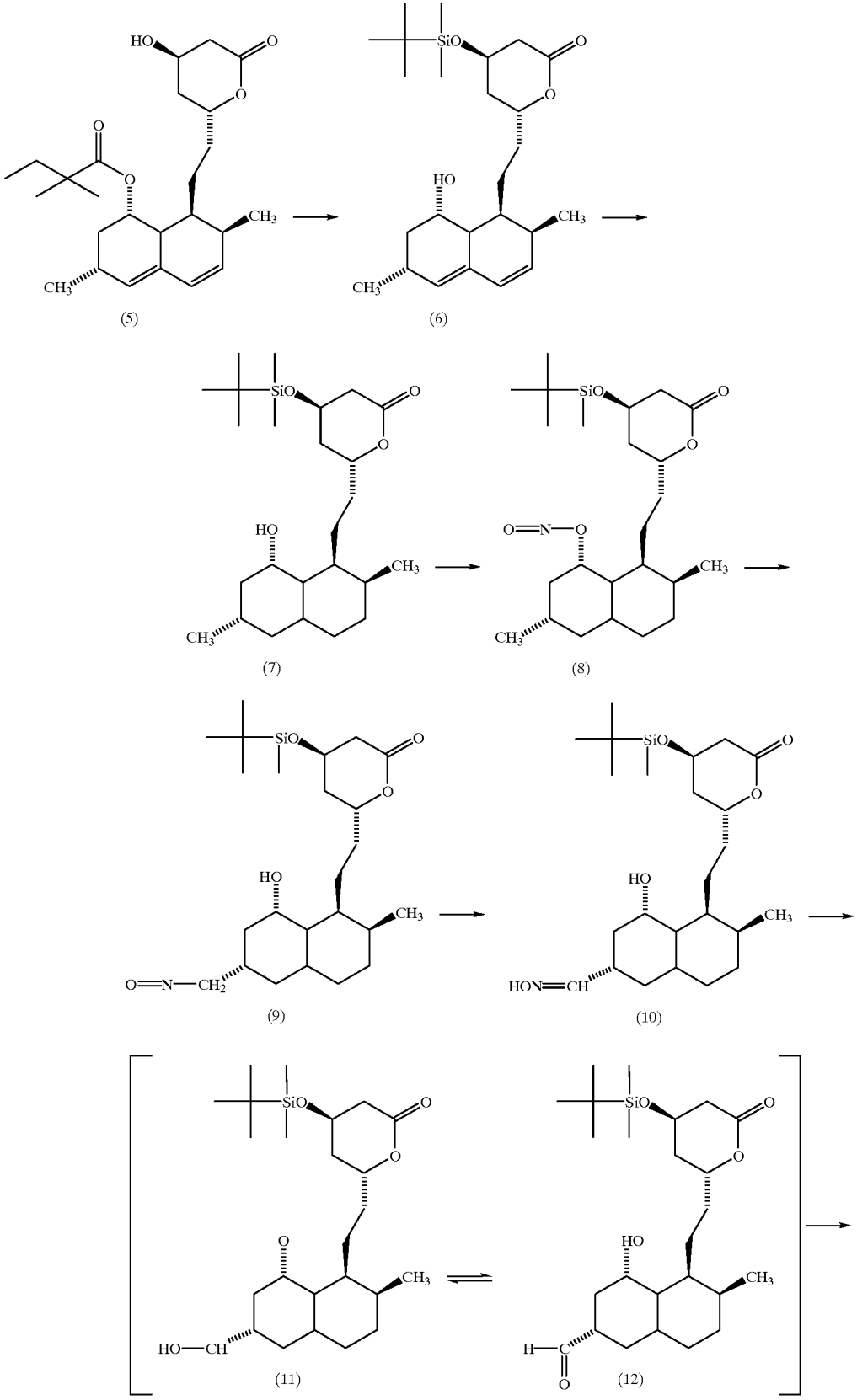
HO
O
O
O
O
CH3
CH3
(5)
SiO
O
O
HO
CH3
CH3
(6)
SiO
O
O
HO
CH3
CH3
(7)
SiO
O
O
O=N—O
CH3
CH3
(8)
SiO
O
O
HO
CH3
O=N—CH2
(9)
SiO
O
O
HO
CH3
HON=CH
(10)
SiO
O
O
O
CH3
HO—CH
(11)
SiO
O
O
HO
CH3
H—C
O
(12)

-continued

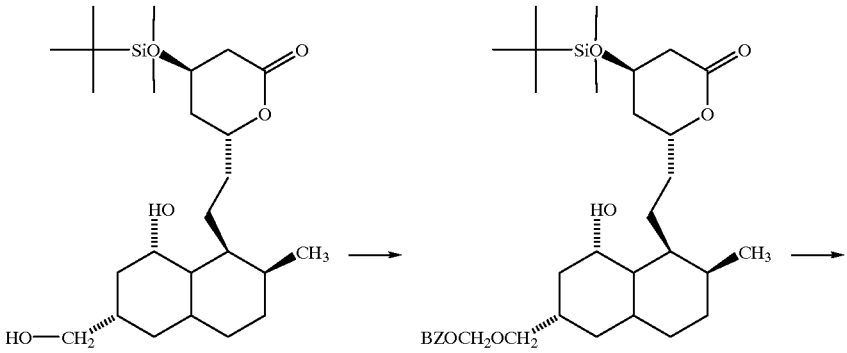

(13) (14)

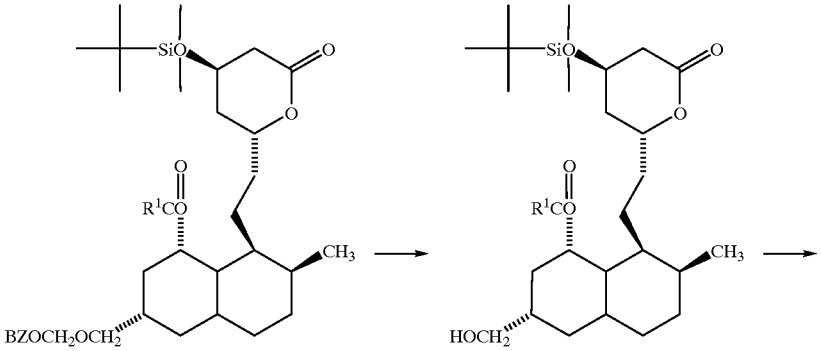

(15) (16)

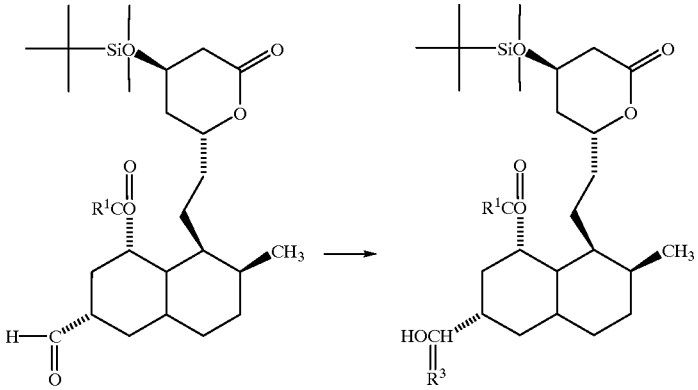

(17) (18)

The starting material, lovastatin (5) is readily available or may be prepared according to the fermentation procedures disclosed in U.S. Pat. No. 4,231,938. The compound of the formula (5) is hydrolyzed under the conditions disclosed in U.S. Pat. No. 4,444,784 and then the 4-hydroxy function in the lactone moiety is protected with a suitable protecting group, exemplified here as a t-butyldimethylsilyl group, according to the procedure disclosed in U.S. Pat. No. 4,444,784 to yield the compound (6). Compound (6) is then hydroqenated under the analogous conditions disclosed in U.S. Pat. No. 4,351,844 to afford the compound (7). Compound (7) is then treated with nitrosyl chloride in the presence of a base, such as a trialkylamine, specifically, trimethylamine, triethylamine, pyridine, N,N-dimethylbenzylamine and the like, to afford the compound (8). Compound (8) is then subjected to a photorearrangement to give the compound (9). Compound (9) is heated to reflux in a protic solvent such as isopropanol and the like to yield the compound (10). Compound (10) is converted into compound (11) by treatment with an alkali metal nitrite, such as sodium nitrite or potassium nitrite, in an aqueous organic acid such as acetic acid, propionic acid or the like. Compound (11), which is a hemiacetal, is in equilibrium with the hydroxy aldehyde, compound (12). This equilibrium mixture of compound (11) and compound (12) is treated with a reducing agent, such as sodium borohydride, to afford compound (13). Compound (13), is converted to compound (14) by treatment with benzyl chloromethyl ether in the presence of a suitable base such as a trialkylamine, preferably diisopropylethylamine, in a suitable organic solvent such as methylene chloride in the cold, preferably at about 0° C. Compound (14) is acylated under suitable conditions utilizing the appropriate alkanoyl halide or alkanoic acid to afford compounds (15). Removal of the benzyloxymethyl protecting group from compounds (15) via catalytic hydrogenation under standard conditions provides compounds (16). The latter are oxidized to compounds (17) by standard methods, including the method of Swern involving the use of oxalyl chloride and dimethyl sulfoxide in methylene chloride followed by triethylamine. Compound (17) is then reacted with an appropriately substituted Grignard reagent to afford compound (18) which after removal of the trialkylsilyl ether protecting group under standard conditions yields the compounds of formula (I) wherein R is

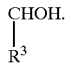

The compounds of formula (I) wherein R is

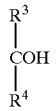

are conveniently prepared from compound (18) by oxidizing the hydroxyalkyl group to the ketone of the structure

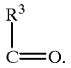

followed by a second Grignard reaction and the removal of the trialkylsilyl ether protecting group.

The compounds of the formula (I) wherein R is $CO_2H$ are conveniently prepared from the corresponding hydroxymethyl containing compound under mild oxidation conditions. The compounds of the formula (16) are treated with tris (triphenylphosphine) ruthenium (II) chloride to afford the 6-formyl derivative which is then treated with sodium chlorite and sulfamic acid to give the desired products.

The compounds of the formulae (I) and (II) wherein a represents a double bond are conveniently prepared from the compound of the formula (6) by the hydrogenation procedure using Wilkinson's catalyst as disclosed in U.S. Pat. No. 4,444,784 and subjecting the resultant 6(R)-[2-[8(S)-hydroxy-2(S)6(R)-dimethyl-1,2,3,4,6,7,8,8a(R)-octahydronaphthyl-1(S)]ethyl]-4(R)-(t-butyldimethylsilyloxy)-3,4,5,6-tetrahydro-2H-pyran-2-one to the above noted reaction sequence. Alternatively a hydrogenation procedure employing a homogenous rhodium catalyst in an alcoholic solvent as described in Ser. No. 092,804 filed Sept. 3, 1987 may be used.

The compounds of the formulae (I) and (II) wherein b represents a double bond are conveniently prepared using an analogous reaction sequence but utilizing 6(R)-[2-[8(S)-hydroxy-2(S),6(S)-dimethyl-1,2,3,5,6,7,8,8a(R)-octahydronaphthyl-1(S)]ethyl]-4(R)-(t-butyldimethylsilyloxy)-3,4,5,6-tetrahydro-2H-pyran-2-one in place of the compound of the formula (7). This starting material may be prepared according to the procedures disclosed in U.S. Pat. No. 4,444,784. Alternatively the starting material may be prepared following the hydrogenation procedure detailed in Ser. No. 092,803 filed Sept. 3, 1987.

The compounds of the formulae (I) and (II) wherein c is a double bond are conveniently prepared using an analogous reaction sequence but utilizing 6(R)-[2-[8(S)-hydroxy-2(S),6(S)-dimethyl-1,2,4a(R),5,6,7,8,8a(S)-octahydronaphthyl-1(S)]ethyl]-4(R)-(t-butyldimethylsilyloxy)-3,4,5,6-tetrahydro-2H-pyran-2-one in place of the compound of the formula (7). This starting material may be prepared from the natural fermentation product prepared according to the procedures disclosed in U.S. Pat. No. 4,294,846. Alternatively this starting material may be prepared by the employment of a homogenous rhodium or iridium catalyst as detailed in copending U.S. patent application Ser. No. 092,802 filed Sept. 3, 1987.

The compounds (17), which are prepared as illustrated in the preceeding synthetic pathway, each have the CHO group appended to the polyhydronaphthalene ring as a 6α-substituent. The corresponding 6β-epimers are conveniently prepared via the following synthetic pathway:

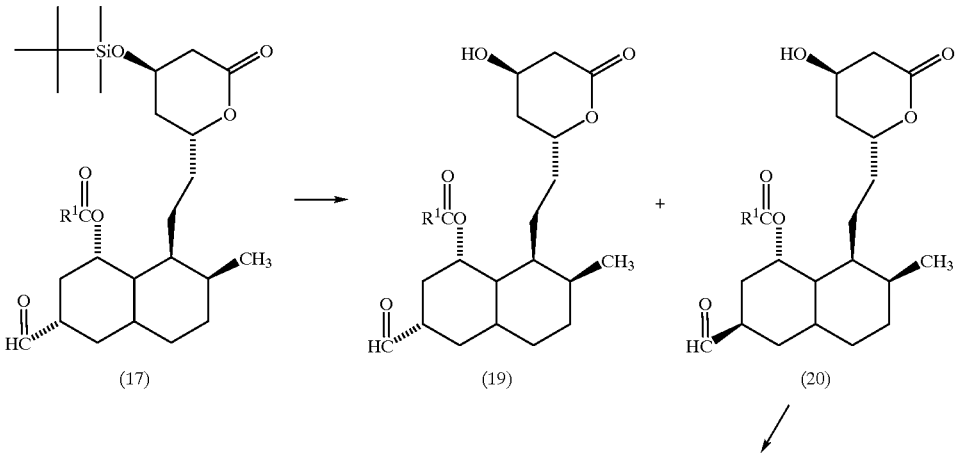

-continued

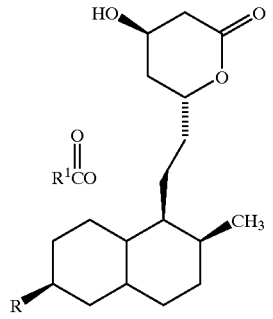

Treatment of compounds (17) under the conditions (i.e., tetra-n-butylammonium fluoride in THF buffered with HOAc) used to deblock the tert-butyldimethylsilyl ether serves both to deblock this protecting group in compounds (17) and to epimerize the resulting 6α-aldehydes (I9) to afford a mixture of epimeric compounds (19) and (20), the ratio of the 6β-epimer to the 6α-epimer being determined by the exact reaction conditions used in each instance. After isolation by chromatography on a suitable support such as silica gel and the like, compounds (20) can be selectively protected on the lactone hydroxy group, as e.g. a silyoxy ether, and then converted to compounds of this invention by utilizing analogous reaction conditions as those employed with the transformations of compound (17) and (18).

Epimerization can also be carried out employing aluminum isoproxide and aluminum oxide to form the β-hydroxymethyl compound following the procedure in Ser. No. 161,529 filed Feb. 29, 1988.

Alternatively, the appropriate dihydro or tetrahydro derivative of mevinolin may be subjected to one of the microbiological methods described above to afford the compounds of the formulae (I) and (II), wherein R is $CH_2OH$ or $CO_2H$.

Where the product formed by the above described synthetic pathways is not the desired form of that compound, then that product may be subjected to one or more further reactions such as hydrolysis, salification, esterification, acylation, ammonolysis or lactonization by conventional methods, as described in more detail hereafter.

The starting compound may be a free carboxylic acid, its corresponding lactone or a salt (e.g., metal, amino acid or amine salt) or ester (particularly alkyl ester) thereof.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, histidine, α,β-diaminobutyric acid or ornithine.

Preferred amines to form amine salts include t-octylamine, dibenzylamine, dichlorohexylamine, morpholine, alkyl esters of D-phenylglycine and D-glucosamine. Also preferred is ammonia to form the ammonium salt.

Esters are preferably the alkyl esters, such as the methyl, ethyl, propyl, isopropyl, butyl, isobutyl or pentyl esters, of which the methyl ester is preferred. However, other esters such as phenyl $C_{1-5}$alkyl, dimethylamino-$C_{1-5}$alkyl, or acetylamino-$C_{1-5}$alkyl may be employed if desired.

Of the starting materials, the alkali metal salts, e.g., the sodium or potassium salts, are particularly preferred, the sodium salt being most preferred as it has been found that this gives the best conversion of the substrate into the desired product.

Where the product obtained by the processes of the present invention is a salt of the carboxylic acid of formula (II), the free carboxylic acid itself can be obtained by adjusting the pH of the filtrate to a value of 4 or less, preferably to a value of from 3 to 4. Any organic acid or mineral acid may be employed, provided that it has no adverse effect upon the desired compound. Examples of the many acids which are suitable include trifluoroacetic acid, acetic acid, hydrochloric acid and sulphuric acid. This carboxylic acid may itself be the desired product or it may be, and preferably is, subjected to subsequent reactions, as described below, optionally after such treatments as extraction, washing and lactonization.

Metal salts of the carboxylic acids of formula (II) may be obtained by contacting a hydroxide, carbonate or similar reactive compound of the chosen metal in an aqueous solvent with the carboxylic acid of formula (II). The aqueous solvent employed is preferably water, or it may be a mixture of water with an organic solvent, preferably an alcohol (such as methanol or ethanol). a ketone (such as acetone), an aliphatic hydrocarbon (such as hexane) or an ester(such as ethyl acetate). It is preferred to use a mixture of a hydrophilic organic solvent with water. Such reactions are normally conducted at ambient temperature but they may, if desired, be conducted with heating.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by a salt exchange reaction.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an ion exchange resin. The solvent employed for this reaction is not critical, provided that it does not adversely affect the reaction; suitable solvents include benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. All of the reactions for producing esters are preferably effected at about ambient temperature, but, if required by the nature of the reaction system, the reactions may be conducted with heating.

The compounds of formula (I) in which R is

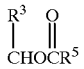

may be prepared from the compounds of formula (I) in which R is

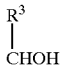

by the treatment of tert-butyldimethylsilyl in the presence of an organic base to afford the compounds in which the hydroxy group of the lactone of the compounds of formula (I) are protected as a tert-butyldimethylsilyl ether. Subsequent acylation using the appropriate acyl halide, anhydride, isocyanate or carbamoyl chloride, under standard conditions. Desilylation under standard conditions will afford the compounds of formula (I) in which R is

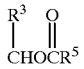

The compounds of formula (I) in which R is $CO_2R^6$ may be prepared from the compounds of formula (I) in which R is $CO_2H$ by treatment with a diazoalkane such as trimethylsilyldiazomethane in a suitable organic solvent such as ether, hexane and the like. Other methods for preparing these ester derivatives involve first protecting the lactone hydroxyl group with a suitable protecting group such as the tert-butyldimethylsilyl or tetrahydropyranyl groups under standard conditions (vida supra) followed by activation of the $CO_2H$ group using standard procedures such as conversion to the acid chloride with oxalyl chloride or treatment with N,N-dicyclohexylcarbodiimide and subsequent reaction with the appropriate alcohol $R^6OH$. Finally, removal of the lactone hydroxyl protecting group will afford the compounds of formula (I) in which R is $CO_2R^6$.

The compouds of the formula (I) in which R is

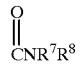

may be prepared from the compounds of formula (I) in which R is $CO_2H$ by activation of the $CO_2H$ group using standard procedures such as treatment with carbonyl diimidazole or with isobutyl chloroformate in such organic solvents such as methylene chloride, THF and the like followed by treatment with $R^7R^8NH$ hydrochloride in the first instance and $R^7R^8NH$ and a suitable base such as triethylamine in the second instance. Alternatively, the lactone hydroxyl group may be protected with a suitable protecting group (vida supra), the $CO_2H$ group converted to the acid chloride and reacted with the desired amine of the formula $R^7R^8NH$ and the lactone hydroxyl protecting group removed to afford the desired amide derivatives of formula (I) in which R is

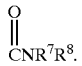

Finally, the subclass of compounds of formula (I) wherein R is

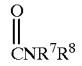

and either $R^7$ or $R^8$ is alkyl or cycloalkyl and the other is N-(substituted) aminocarbonyl is prepared by treating the requisite compound of formula (I) in which R is $CO_2H$ with a carbodiimide of the formula $R^7N—C—NR^8$ in the absence of extraneous nucleophiles and allowing the intially formed imino anhydride to undergo intramolecular rearrangement to the desired acylurea.

Lactones of the carboxylic acids of formula (I) may be obtained by lactonizing the carboxylic acids of formula (II) under ordinary conditions known to one skilled in the art.

The compounds of this invention are useful as antihypercholesterolemic agents for the treatment of arteriosclerosis, hyperlipidemia familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)imino-trimethylene dihalide]. The relative amounts of the compounds of this invention and these polymers is between 1:100 and 1:15,000.

The intrinsic HMG-CoA reductase inhibition activity of the claimed compounds is measured in the in vitro protocol published in J. Med. Chem., 28, p. 47–358 (1985) and described below:

Isolation of HMG-CoA Reductase

Male Holtzman Sprague-Dawley rats (225–250 g) were kept on reversed lighting and fed Purina rat chow containing 3% cholestyramine for 7 days preceding their sacrifice by $CO_2$ asphyxiation. Livers were removed 6 hours into the dark cycle and used immediately to prepare microsomes. HMG-CoA reductase was solubilized from the freshly prepared microsomes by the method of Heller and Shrewsbury [J. Biol. Chem., 1976, 251, 3815]and purified through the second ammonium sulfate precipitation step as described by Kleinsek et al. [Proc. Natl. Acad. Sci. USA, 1977, 74, 1431]. The enzyme preparation was tested for HMG-CoA reductase potency and diluted with 100 mM phosphate buffer (pH 7.2) so that 100 $\mu$l of the enzyme solution, when added to the assay control, gave a value of 50,000–60,000 dpm. The enzyme preparation was stored at –80° C.

HMG-CoA Reductase Inhibition Assay

The assay is essentially the procedure of Shefer et al. [J. Lipid Res., 1972, 13, 402]. The complete assay medium contained the following in a total volume of 0.8 ml: phosphate buffer, pH 7.2, 100 mM; $MgCl_2$, 3 mM; NADP, 3 mM; glucose-6-phosphate, 10 mM; glucose-6-phosphate dehydro-genase, 3 enzyme units; reduced glutathione 50 mM; HMG-CoA (glutaryl-3-$^{14}$C, New England Nuclear), 0.2 mM (0.1 $\mu$Ci); and partially purified enzyme stock solution, 100 $\mu$L.

Test compounds or compactin, after first being converted to the sodium salt of their dihydroxy acid form in situ by addition of 1N NaOH (1 equivalent), were added to the assay system in 10-$\mu$L volumes at multiconcentration levels. After a 40-minute incubation at 37° C. with shaking and exposure to air, the reaction was stopped by the addition of 0.4 mL of 8 N HCl. After an additional 30-minute incubation period at 37° C. to ensure the complete lactonization of mevalonic acid to mevalonolactone, 0.2 ml of the mixture was added to an 0.5×5.0 cm column containing 100–200 mesh Bio-Rex 5, chloride form (Bio-Rad), wetted with distilled water, as described by Alberts et al. [Proc. Natl. Acad. Sci. U.S.A., 1980, 77, 3967]. The unreacted [$^{14}$C] HMG-CoA was absorbed on the resin and the [$^{14}$C]mevalonolactone was eluted with distilled water (2×1 ml) directly into 7-ml scintillation vials. Five milliliters of Aquasol-2 (New England Nuclear) was added to each vial, and radioactivity was measured in a Packard Tri Carb Prias scintillation counter. $IC_{50}$ values were determined by plotting percentage inhibition against test compound concentration and fitting a straight line to the resulting data by using the least-squares method. For estimation of relative inhibitory potencies, compactin was assigned a value of 100 and the $IC_{50}$ value of the test compound was compared with that of compactin determined simultaneously.

Representative of the intrinsic HMG-CoA reductase inhibitory activities of the claimed compounds are the relative potencies tabulated below for a number of the claimed compounds.

TABLE I

| Compounds of the Formula (II) wherein $R^2$ = H | | | | | | Relative |
|---|---|---|---|---|---|---|
| a | b | c | AS* | R | $R^1$ | Potency[1] |
| db | — | db | S | $CH_2OH$ | 1,1-dimethylpropyl | 189 |
| db | — | db | S | $CO_2H$ | 1,1-dimethylpropyl | 99 |
| db | — | db | R | $CO_2H$ | 1,1-dimethylpropyl | 94 |
| db | — | db | S | $CO_2H$ | sec-butyl | 26 |
| db | — | db | R | $CH_2OH$ | sec-butyl | 47 |
| db | — | db | S | $CONMe_2$ | 1,1-dimethylpropyl | 82 |
| db | — | db | S | $CONEt_2$ | 1,1-dimethylpropyl | 65 |
| db | — | db | S | $CH_2OC(=O)NHPh$ | 1,1-dimethylpropyl | 726 |
| db | — | — | R | $CH_2OH$ | 1,1-dimethylpropyl | 213 |
| db | — | — | R | 2,2-dimethyl-butyryloxy-methyl | 1,1-dimethylpropyl | 33 |
| — | — | — | S | $CH_2OH$ | 1,1-dimethylpropyl | 86 |
| — | — | — | S | $CH_2OH$ | cyclohexyl | 33 |
| — | — | — | S | $CO_2H$ | 1,1-dimethylpropyl | 79 |
| — | — | — | S | 2,2-dimethyl-butyryloxy-methyl | 1,1-dimethylpropyl | 100 |
| — | — | — | S | $CONMe_2$ | 1,1-dimethylpropyl | 75 |
| — | — | — | S | $CONH_2$ | 1,1-dimethylpropyl | 107 |
| — | — | — | S | CHOHPH | 1,1-dimethylpropyl | 220 |
| — | — | — | S | $CHOHCH_3$ (ISOMER A) | 1,1-dimethylpropyl | 131 |
| — | — | — | S | $CHOHCH_3$ (ISOMER B) | 1,1-dimethylpropyl | 113 |
| — | — | — | R | $CHOHCH_3$ (ISOMER A) | 1,1-dimethylpropyl | 111 |
| — | — | — | R | $CHOHCH_3$ (ISOMER B) | 1,1-dimethylpropyl | 104 |
| — | — | — | S | $CO_2Et$ | 1,1-dimethylpropyl | 125 |
| — | — | — | S | $CO_2$i-Pr | 1,1-dimethylpropyl | 80 |

TABLE I-continued

| Compounds of the Formula (II) wherein $R^2$ = H | | | | | | Relative |
|---|---|---|---|---|---|---|
| a | b | c | AS* | R | $R^1$ | Potency[1] |
| — | — | — | S | O O<br>‖ ‖<br>CONCNH-Cyclohexyl<br>\|<br>Cyclohexyl | 1,1-dimethylpropyl | 100 |

[1]Relative to compactin arbitrarily assigned a value of 100
*AS = absolute sterochemistry of the methine moiety to which R is appended
db = double bond
— = single bond Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

The following media are utilized in the bioconversion reactions described below:

| | Grams per liter distilled water |
|---|---|
| Medium A | |
| Yeast extract | 4.0 |
| Malt extract | 10.0 |
| Nutrient broth | 4.0 |
| Dextrose | 4.0 |
| pH 7.4 | |
| Medium sterilized for 20 min. at 121° C. | |
| Medium B | |
| Dextrose | 10.0 |
| Polypeptone | 2.0 |
| Meat extract | 1.0 |
| Corn steep liquor | 3.0 |
| pH 7.0 | |
| Medium sterilized for 20 min. at 121° C. | |

I. Culture Conditions and Bioconversion

A lyophilized tube of Nocardia autotrophica subsp. canberrica ATCC 35204 (MA-6180) was used to inoculate 18×175 agar slants (Medium A) which were incubated at 27° C. for 7 days. The slant culture was washed with 5 ml of sterile medium B and transferred to a 250 ml flask containing 50 ml of sterile medium B. This first stage seed was grown at 27° C. on a 220 rpm shaker and, after 24 hours, 2 ml was transferred to another flask of sterile medium B.

Grown under the above conditions, the second seed was used to start the bioconversion culture: 20 ml of the seed culture was placed in 400 ml of sterile medium B in a 2L flask. After the culture had grown for 24 hours, 80 mg of the sodium salt of 7-[1,2,6,7,8,8a(R)-hexahydro-2(S),6(R)-dimethyl-8(S)-(2,2-dimethylbutyryloxy)-1(S)-naphthyl]-3(R),3(R)-dihydroxyheptanoic acid was added to each flask. The incubation was continued for 28 hours or until no 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid could be detected by HPLC. The whole broth was clarified by centrifugation followed by filtration through Whatman No. 2 filter paper.

II. HPLC Methods

Aliquots of whole broth could be analyzed for 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid derivatives by HPLC. Filtered broth could be injected directly (10 to 20 $\mu$l) or after dilution with methanol. The compounds were separated on reversed phase columns utilizing a gradient of 35 to 45 percent aqueous acetonitrile at flow rates ranging between 1 and 3 ml/min. Addition of glacial acetic acid or $H_3PO_4$ (0.1 ml/L mobile phase) was required for the separation of the free acids. Derivatives of 7-[1,2,6,7,8,8a(R)-hexahydro-2(S),6(R)-dimethyl-8(S)-(2,2-dimethylbutyryloxy)-1(S)-naphthyl]-3-(R),5(R)-dihydroxyheptanoic acid were detected by monitoring the absorbance at 238 nm, as well as the absorbance ratio of 238 nm/228 nm. The Waters HPLC system included a WISP auto-injector, model 710B equipped with models 510 and 590 pumps, a model 490 UV-visible detector, and the 840 data system. A number of columns were used successfully for the separations, including the following: Waters $\mu$ Bondapak-C18, Altex Ultrasphere-C18, Rainin Microsorb-C18 and a Brownlee MPLC-C8.

III. Methyl 7-[1,2,6,7,8,8a(R)-hexahydro-6(S)-hydroxymethyl-2(S)-methyl-8(S)-(2,2-dimethylbutyryloxy)-1(S)-naphthyl]-3(R),5(R)-dihydroxyheptanoate.

The whole broth of three X 400 ml culture broth was combined and filtered through celite and Whatman No. 2 filter paper. The filtrate was acidified to pH 5.0 with 25 percent $H_3PO_4$ and then extracted with three, 700 ml-portions of ethyl acetate. Following concentration under vacuum (25° C.), the organic solution was extracted with four volumes of 0.1% $NaHCO_3$. The bicarbonate solution was slowly adjusted to pH 4.5 with ethyl acetate which was subsequently concentrated to 100 ml in vacuo. The concentrate was combined with 150 ml of diethyl ether containing an excess of $CH_2N_2$ and stirred overnight for preparation of the methyl ester derivatives. Evaporation of the ether was performed under a stream of nitrogen and the remaining solution was washed with 100 ml of phosphate buffer, pH 7.0. The organic phase was taken to dryness in vacuo and the resulting residue was dissolved in a minimum of isopropanol. Final purification of methyl 7-[1,2,6,7,8,8a(R)-hexahydro-6(S)-hydroxymethyl-2(S)-methyl-8(S)-(2,2-dimethylbutyryloxy)-1(S)-naphthyl]-3(R),5(R)-dihydroxyheptanoate was accomplished by HPLC utilizing a Waters $\mu$Bondapak-C18 column (1×30 cm). The mobile phase was 34 percent aqueous $CH_3$3 CN at 4 ml/min. Methyl 7-[1,2,6,7,8,8a(R)-hexahydro-6(S)-hydroxymethyl-2(S)-methyl-8(S)-(2,2-dimethylbutyryloxy)-1(S)-naphthyl]-3(R),5(R)-dihydroxyheptanoate had a retention time at 31 minutes. After evaporation of the solvent, the sample was dried under vacuum for 24 hours to afford the title compound which was identified by NMR. $1_H$ nmr ($CDCl_3$) δ 0.83 (3H, t, J=7 Hz), 0.89 (3H, d, J=7Hz), 1.107 (3H, s), 1.111 (3H, s), 2.16 (H, m), 3.51 (H, d of d, J=5.5, 10.5 Hz), 3.61 (H, d of d, J=5.5, 10.5 Hz), 3.69 (3H,s), 3.77 (H, m), 4.22 (H, m) 5.36 (H, bs), 5.50 (H, bs), 5.80 (H, d of d, 6, 9.5 Hz), 6.00 (H, d, J=9.5 Hz).

IV. Isolation of 6(R)-[2-[8(S)-(2,2-Dimethylbutyryloxy)-6(R)-carboxy-2(S)-methyl-1,2,6,7,8,8a(R)-hexahydronaphthyl-1(S)]ethyl]-4(R)-hydroxy-3,4,5,6-tetrahydro-2H-pyran-2-one and 6(R)-[2-(8(S)-(2,2-Dimethylbutyryloxy)-6(S)-carboxy-2(S)-methyl-1,2,6,7,8,8a(R)-hexahydronaphthyl-1(S)]ethyl]-4(R)-hydroxy-3,4,5,6-tetrahydro-2H-pyran-2-one.

The whole broth (1200 ml) was clarified as before and then adjusted to pH 3.5 with $H_3PO_4$. The filtrate was loaded on a HP-20 column (3×50 cm) which had been equilibrated with water containing 0.1 percent $CH_3COOH$. After washing the column with 1 L of water and 1 L of 25 percent $CH_3CN$, the products were eluted with 600 ml of 50 percent $CH_3CN$. The acetonitrile was removed under vacuum at 35° C. The water was taken to pH 8.0 with NaOH and washed with two 500 ml portions of $CH_2Cl_2$ which was discarded. After readjusting the pH to 3.5 with $H_3PO_4$, the derivatives were first extracted into 1.8 L ethyl acetate and then back-extracted into 1 L of 1 percent $NaHCO_3$. The bicarbonate solution was acidified to pH 5 with acetic acid and loaded on a HP-20 column (1.5×50 cm). Once the column was washed with 700 ml of $H_2O$ followed by 700 ml of 30 percent $CH_3CN$, the column was eluted with a gradient of 30 to 50 percent $CH_3CN$. The fractions were monitored by UV absorbance (228, 238, 248 nm) and by HPLC. Crude 6(R)-[2-[8(S)-(2,2-dimethylbutyryloxy)-6(S)-carboxy-2(S)-methyl-1,2,6,7,8,8a(R)-hexahydronaphthyl-1(S)]ethyl]4(R)-hydroxy-3,4,5,6-tetrahydro-2H-pyran-2-one was collected at about 40 percent $CH_3CN$.

After removing the solvent in vacuo, the resulting residue was sonicated with 20 ml of toluene for 10 minutes, 3 μl of $CF_3COOH$ was added and the mixture was heated for 30 minutes at 70° C. The toluene was removed under vacuum at 70° C. and the resulting residue was dissolved in 300 μl of $CH_3CN$. The preceding procedure was employed to convert the derivative of 7-[1,2,6,7,8,8a(R)-hexa- hydro-2(S),6(R)-dimethyl-(b 2,2-dimethylbutyryloxy)-1(S)-naphthyl]-3(R),5(R)-dihydroxyheptanoic acid to its lactone form for ease of isolation. Final purification was accomplished by HPLC using an Altex-C8 column (1×25 cm) and a gradient of $CH_3CN/CH_3OH/H_2O/CH_3COOH$ (20/30/50/0.01 to 25/30/45/0.01) at 2.7 ml/min. 6(R)-[2-[8(S)-(2,2-Dimethylbutyryloxy)-6(S)-carboxy-2(S)-methyl-1,2,6,7,8,8a(R)-hexahydronaphthyl-1(S)]ethyl]-4(R)-hydroxy-3,4,5,6-tetrahydro-2H-pyran-2-one had a retention time of 30 to 31 minutes and was identified by NMR. $1_H$ nmr ($CDCl_3$) δ 0.82 (3H, t, J=7.5 Hz), 0.88 (3H, d, J=7 Hz), 1.11 (6H, s), 1.53 (H, m), 2.60 (H, m) 2.72 (H, d of d, J=5, 18 Hz), 3.29 (H, m), 4.365 (H, m), 4.60 (H, m), 5.39 (H, bs), 5.62 (H, bs), 5.83 (H, d of d, J=6, 10 Hz), 6.00 (H, d, J=10 Hz)

An alternate final purification involved fractionation by preparative HPLC using a Vydac C-18 column and eluting with 0–60% $CH_3CN$/0.170 phosphoric acid. Application of this purification technique to a partially-purified mixture of acidic materials (200 mg) afforded fractions A containing a less polar, major component and fractions B containing a more polar, minor component. Concentration of fractions A in vacuo to remove the bulk of the $CH_3CN$ gave an aqueous mixture which was extracted with chloroform. The organic extract was washed with saturated brine, dried ($Na_2SO_4$), filtered and evaporated in vacuo to provide 6(R)-[2-[8(S)-(2,2-dimethylbutyryloxy)-2(S)-methyl-6(S)-carboxy-1,2,6,7,8,8a(R)-hexanaphthyl-1(S)]ethyl]-4(R)-hydroxy-3,4,5,6-tetrahydro-2H-pyran-2-one as a colorless solid, mp 167°–170° C.; $1_H$ nmr ($CD_3CN$) δ 6.04 (H, d, J=9.8 Hz), 5.88 (H, d of d, J=9.7, 6.0 Hz), 5.62 (H, m), 5.33 (H, m), 4.56 (H, m), 4.23 (H, m), 3.23 (H, m), 2.62 (H, d of d, J=17.4, 4.8 Hz), 2.44 (H, d of d of d, J=17.5, 3.7, 1.6 Hz), 1.12 (6H, s), 0.90 (3H, d, J=7.1 Hz), 0.83 (3H, t, J=7.5 Hz). Recrystallization of this 6β-carboxy isomer from EtoAc-Hexane did not alter the mp. Furthermore, this 6β-carboxy isomer mp 167°–170° C., could be obtained directly from the partially-purified mixture of acidic materials (vida supra) by crystallization from di-n-butyl ether.

Anal. Calc'd for $C_{25}H_{36}O_7$: C, 66.94; H, 8.09. Found: C, 66.66; H, 8.41.

From fractions B (vida supra) there was obtained the corresponding 6α-carboxy isomer 6(R)-[2-[8(S)-(2,2-dimethylbutyryloxy)-2-(S)-methyl-6(R)-carboxy-1,2,6,7,8,8a(R)-hexahydronaphthyl-1(S)]ethyl]-4(R)-hydroxy-3,4,5,6-tetrahydro-2H-pyran-2one, as a colorless solid, mp 189°–194° C.; 1 H nmr ($CD_3CN$) δ 6.06 (H, d, J=9 Hz), 5.88 (H, d of d, J=9.5, 5.9 Hz), 5.71 (H, m), 5.24 (H, m), 4.51 (H, m), 4.21 (H, m), 3.20 (H, m), 2.70 (H, m), 2.62 (H, d of d, J=17.4, 4.8 Hz), 2.44 (H, m), 1.06 (H, s), 1.03 (3H, s), 0.89 (3H, d, J=7.0 Hz), 0.82 (3H, t, J=7.5 Hz).

Anal Calc'd for $C_{25}H_{36}O_7$: C, 66.94; H, 8.09. Found: C, 66.70; H, 8.38.

In a similar fashion Nocardia autotrophica subsp. canberrica ATCC 35203 (MA6181) was utilized in the bioconversion reaction with the sodium salt of 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid to afford the desired products.

Additionally, the sodium salt of 7-[1,2,6,7,8,8a(R)-hexahydro-2(S),6(R)-dimethyl-8(S)-(2-methylbutyryloxy)-1(S)-naphthyl]-3(R),5(R)-dihydroxyheptanoic acid, the sodium salt of ring opened mevinolin, was subjected to analogous bioconversion reactions utilizing both N. autotrophic subsp. amethystina ATCC 35204 (MA6180) and N. autotrophic subsp. canberrica ATCC 35203 (MA6181) to predominantly afford 6(R)-[2-[8(S)-(2-methylbutyryloxy)-6(S)-carboxy-2(S)-methyl-1,2,6,7,8,8a(R)-hexahydronaphthyl-1(S)]ethyl]-4(R)-hydroxy-3,4,5,6-tetrahydro-2H-pyran-2-one and methyl 7-[1,2,6,7,8,8a(R)-hexahydro-6(S)-hydroxymethyl-2(S)-methyl-8(S)-(2-methylbutyryloxy)-1(S)-naphthyl]-3(R),5(R)-dihydroxyheptanoate, respectively.

EXAMPLE 2

Preparation of 6(R)-[2-[8(S)-(2,2-dimethylbutyryloxy)-2(S)-methyl-6(S)-hydroxymethyl-1,2,3,4,4a(S),5,6,7,8,8a(S)-decahydronaphthyl-1(S)]ethyl]-4(R)-hydroxy-3,4,5,6-tetrahydro-2H-pyran-2-one (a) 6(R)-[2-[8(S)-Nitrosyloxy-2(S),6(S)-dimethyl-1,2,3,4,4a(S),5,6,7,8,8a(S)-decahydronaphthyl-1(S)]ethyl]-4(R)-(tert-butyldimethylsilyloxy)-3,4.5.6-tetrahydro-2H-pyran-2-one (2a)

A stream of nitrosyl chloride gas was passed into a stirred solution of 6(R)-[2-[8(S)-hydroxy-2(S), 6(S)-dimethyl-1,2,3,4,4a(S),5,6,7,8,8a(S)-decahydro-naphthyl-1(S)]ethyl]-4(R)-(tert-butyldimethylsilyloxy)-3,4,5,6-tetrahydro-2H-pyran-2-one (800 mg, 1.82 mmol) in pyridine (14 ml) at 0° C. until the solution was saturated (brownish fumes filled the reaction flask). The resulting mixture was stirred at 0° C. for another 10 minutes, poured into cold water and extracted with diethyl ether. The extract was washed successively with dilute HCl, water and 5% $NaHCO_3$, dried ($MgSO_4$), filtered and concentrated in vacuo to afford the title compound as a white solid; mp 92°–4° C.; $1_H$ nmr ($CDCl_3$) δ 0.86 (3H, d, J=7 Hz), 0.89 (9H, s), 0.99 (3H, d, J=7 Hz), 2.55 (H, m of d, J=18 Hz), 2.60 (H, d of d, J=18,4 Hz), 4.28 (H, m), 4.53 (H, m), 5.84 (H, m).

Anal Calc'd for $C_{25}H_{45}NO_5Si$: C, 64.20; H, 9.70; N, 3.00. Found: C, 64.09; H, 10.00; N, 3.06.

(b) 6(R)-[2-[8(S)-Hydroxy-2(S)-methyl-6(S)-nitrosylmethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (2b)

Nitrogen gas was passed through a solution of compound 2a (870 mg, 1.82 mmol) in benzene (320 ml) for 25 minutes. This solution was irradiated under $N_2$ with a 450 watt Hanovia medium pressure mercury lamp (pyrex filter) for 40 minutes at room temperature. The reaction mixture was then concentrated in vacuo and the residue applied to a silica gel column. Elution of the column with methylene chloride:acetone (50:1; v:v) followed by elution with methylene chloride:acetone: isopropanol (100:10:2; v:v:v) yielded the desired product as a foamy oil; $1_H$ nmr ($CDCl_3$) δ 0.83 (3H, d, J=7 Hz), 0.88 (9H, s) 4.10 (H, bs), 4.29 (H, m), 4.64 (2H, d, J=8 Hz), 4.67 (H, m).

(c) 6(R)-[2-[8(S)-Hydroxy-2(S)-methyl-6(S)-hydroxyiminomethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (2c)

Compound 2b (288 mg, 0.616 mmol) was dissolved in isopropanol (15 ml) and heated at reflux for 2 hours. After cooling the reaction mixture was concentrated in vacuo to leave a residue which afforded the title compound as a gummy oil; $1_H$ nmr ($CDCl_3$) δ 0.86 (3H, d, J=7 Hz), 0.90 (9H, s) 2.33 (H, d, J=14 Hz), 2.78 (H, m), 4.11 (H, m), 4,32 (H, m), 4.66 (H, m), 7,50 (H, d, J=6 Hz).

(d) 6(R)-[2-[8-Hydroxy-2(S)-methyl-6(S)-formyl-1,2,3,4,4a(S),5,6,7,8,8a(S)-decahydronaphthyl-1(S)]-ethyl]-4(R)-(tert-butyldimethylsilyloxy)-3,4,5,6-tetrahydro-2H-pyran-2-one (2d)

Sodium nitrite (477 mg 6.83 mmol) was added at 0° C. in one portion to a stirred solution of compound 2c (324 mg 0.683 mmol) in acetic acid (14 ml) and water (7 ml). The resulting mixture was stirred at 0° C. for 10 minutes, warmed to room temperature and stirred for 2.5 hours. The mixture was then diluted with water and extracted with diethyl ether. This ethereal extract was washed with water, 5% $NaHCO_3$ (twice), dried and filtered. Evaporation of the filtrate in vacuo afforded a brownish oily residue whose nmr spectrum is consistent with the structure for compound 2d; $1_H$ nmr ($CDCl_3$) δ 0.80 (3H, d, J=7 Hz), 0.88 (9H, s), 4,30 (H, m) 4.55 (2H, m).

(e) 6(R)-[2-[8(S)-Hydroxy-2(S)-methyl-6(S)-hydroxymethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (2e)

Powdered sodium borohydride (40 mg, 1.05 mmol) was added at 0° C. to a stirred solution of compound 2d (296 mg, 0.651 mmol) in 95% ethanol (15 ml) in one portion. The resulting mixture was stirred at 0° C. for 0.5 hours, then slowly treated with a solution of aqueous $(NH_4)_2SO_4$ (0.7 g in 15 ml of $H_2O$). The resulting mixture was stirred at O° C. for 0.5 hours, diluted with water (60 ml) and extracted with diethyl ether. This extract was washed with water, 5% $NaHCO_3$, dried, filtered and evaporated to give a crude sample which was purified by flash chromatography. Elution of the column with methylene chloride:acetone:isopropanol (100:10:2; v:v:v) afforded the desired product as a white solid; mp 124°–7° C.; $1_H$ nmr ($CDCl_3$) δ 0.83 (3H, d, J=7Hz), 0.90 (9H, s), 3.73 (H, d of d, J=11,6 Hz), 3.79 (H, d of d, J=11,6 Hz), 4.10 (H, bs) 4.31 (H, m), 4.70 (H, m).

Anal Calc'd for $C_{25}H_{46}O_5Si$ C, 66.03; H, 10.20. Found: C, 66.07; H, 10.38.

(f) 6(R)-[2-[8(S)-Hydroxy-2(S)-methyl-6(S)-(tert-butyldiphenylsilyloxymethyl)-1,2,3,4,4a(S),5,6,7,8,8a(S)-decahydronaphthyl-l(S)]ethyl]-4(R)-(tert-butyldimethylsilyloxy)-3,4,5,6-tetrahydro-2H-pyran-2-one (2f)

A solution of tert butyldiphenylsilyl chloride (140 mg, 0.50 mmol) in dimethylformamide (1 ml) was added at 0° C. to a stirred solution of compound 2e (0.150 g, 0.33 mmol) and imidazole (115 mg, 1.7 mmol) in dimethylformamide (4 ml). The resulting mixture was stirred at 0° C. for 15 minutes and then warmed to room temperature and stirred for 15 hours. The mixture was poured into cold water and extracted with diethyl ether. This ethereal extract was washed with dilute HCl and 5% $NaHCO_3$, dried, filtered and evaporated to leave crude product 2f which was purified by flash chromatography on a silica gel column. Elution of the column with methylene chloride:acetone (5:1; v:v) gave the desired product as a gummy oil; $1_H$ nmr ($CDCl_3$) δ 0.84 (3H, d, J=7 Hz), 0.90 (9H, s), 1.09 (9H, s), 2.99 (H, d, J=6 Hz), 3.7–3.85 (2H, m) 4.02 (H, m), 4.30 (H, m) 4.67 (H, m) 7,3–7.5 (6H, m), 7.65–7.8 (4H, m).

(g) 6(R)-[2-[8(S)-(2,2-Dimethylbutyryloxy)-2(S)-methyl-6(S)-(tert-butyldiphenylsilyloxymethyl)-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (2g)

Lithium bromide powder (0.200 g, 2.30 mmol) was added at room temperature under $N_2$ in one portion to a stirred solution of 2,2-dimethylbutyryl chloride (0.150 g, 1.11 mmol) in pyridine (3.5 ml). The resulting mixture was stirred at room temperature until it became a homogenous solution (0.5 hours). 4-Dimethylaminopyridine (DMAP) was added (80 mg, 0.65 mmol). To the resulting mixture was added a solution of compound 2f (229 mg, 0.33 mmol) in pyridine (2.5 ml). The resulting mixture as heated at 90°–95° under $N_2$ for 70 hours. The reaction mixture was cooled, poured into cold water and extracted with diethyl ether. This ethereal extract was washed successively with dilute HCl, water and 5% $NaHCO_3$, then dried, filtered and concentrated in vacuo to afford an oily residue which was purified by flash chromatography on silica gel, eluting with methylene chloride:acetone (200:1; v:v). The product fractions were purified further by preparative tlc (Analtech $SiO_2$ plates, eluant= $CH_2Cl_2$:acetone (75:1; v:v) to give the desired compound as a colorless viscous oil; $1_H$ nmr ($CDCl_3$) δ 0.66 (3H, t, J=7 Hz), 0.84 (3H, d, J=7 Hz), 0.9 (9H, s). 0.91 (6H, s). 1.10 (9H, s) 3.51 (H, d of d, J=11,4 Hz) 3.85 (H, t, J=11 Hz), 4.30 (H, m), 4.55 (H, m), 5.08 (H, m) 7.3–7.5(6H, m) 7.6–7.8 (4H, m).

(h) 6(R)-[2-[8(S)-(2,2-Dimethylbutyryloxy)-2(S)-methyl-6(S)-hydroxymethyl-1,2,3,4,4a(S),5,6,7,8,8a(S)-decahydronaphthyl-l(S)]ethyl]-4(R)-hydroxy-3,4,5,6-tetrahydro-2H-pyran-2one. (2h)

Tetra-n-butylammonium fluoride solution (1 ml, 1 M,1 mmol) was added to a stirred mixture of compound 2g (55 mg, 0.0695 mmol) and acetic acid (0.12 ml, 2.10 mmol) in tetrahydrofuran (1.2 ml). The resulting mixture was stirred at room temperature for 36 hours. The reaction mixture was heated at reflux for 4.5 hours, cooled to room temperature and poured into cold water and extracted with diethyl ether. The ethereal extract was washed with 5% $NaHCO_3$, dried, filtered, and concentrated in vacuo to yield a residue which was purified by flash chromatography on silica gel. Elution of the column with methylene chloride:acetone (10:1; v:v) removed the impurities. Further elution with methylene chloride:acetone:isopropanol (100:10:5; v:v:v) afforded the desired compound as a gummy oil ; $1_H$ nmr ($CDCl_3$) δ 0.85 (3H, d, J=7 Hz), 0.87 (3H, t, J=7 Hz) 1.16 (3H, s), 1.17 (3H, s), 2.62 (H, m of d, J=18 Hz), 2.73 (H, d of d, J=18, 5 Hz), 3.0 (H, bs), 3.57 (H, d of d, J=11,6 Hz), 3.80 (H, t, J=11 Hz) 4.34 (H, m), 4.60 (H, m) 5.20 (H, m).

Anal Calc'd for $C_{25}H_{42}O_6$: C, 68.46; H, 9.65. Found: C, 68.35; H, 9.85.

EXAMPLE 3

Preparation of 6(R)-[2-[8(S) (2,2-dimethylbutyryloxy)- 2-(S)-methyl-6(S)-(1 hydroxyethyl)-1,2,3,4,4a(S),5,6,7,8,8a(S)-decahydronaphthyl-1(S)]ethyl]-4( R)-hydroxy-3,4,5, 6-tetrahydro-2H-pyran-2-one (a) 6(R)-[2-[8(S)-Nitrosyloxy-2(S),6(S)-dimethyl-1,2,3,4,4a (S),5,6,7,8,8a(S)-decahydronaphthyl-1(S)]ethyl]-4(R)-(tert-butyldimethylsilyloxy)-3,4,5,6-tetrahydro-2H-pyran-2-one (3a)

A stream of nitrosyl chloride gas was passed into a stirred solution of 6(R)-[2-[8(S)-hydroxy-2(S)-6(S)-dimethyl-1,2, 3,4,4a(S),5,6,7,8,8a(S)-decahydronaphthyl-1(S)]ethyl]-4 (R)-(tert-butyldimethylsilyloxy)-3,4,5,6-tetrahydro-2H-pyran-2-one (800 mg, 1.82 mmol) in pyridine (14 ml) at 0° C. until the solution was saturated (brownish fumes filled the reaction flask). The resulting mixture was stirred at 0° C. for another 10 minutes, poured into cold water and extracted with diethyl ether. The extract was washed successively with dilute HCl, water and 5% $NaHCO_3$, dried ($MgSO_4$), filtered and concentrated in vacuo to afford the title compound as a white solid; mp 92°–4° C.; $1_H$ nmr ($CDCl_3$) δ 0.86 (3H, d, J=7 Hz), 0.89 (9H, s), 0.99 (3H, d, J=7 Hz), 2.55 (H, m of d, J=18 Hz), 2.60 (H, d of d, J=18,4 Hz), 4.28 (H, m), 4.53 (H, m), 5.84 (H, m).

Anal Calc'd for $C_{25}H_{45}NO_5Si$: C, 64.20; H, 9.70; N, 3.00. Found: C, 64.09; H, 10.00; N, 3.06.

(b) 6(R)-[2-[8(S)-Hydroxy-2(S)-methyl-6(S)-nitrosylmethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (3b)

Nitrogen gas was passed through a solution of compound 3a (870 mg, 1.82 mmol) in benzene (320 ml) for 25 minutes. This solution was irradiated under $N_2$ with a 450 watt Hanovia medium pressure mercury lamp (pyrex filter) for 40 minutes at room temperature. The reaction mixture was then concentrated in vacuo and the residue applied to a silica gel column. Elution of the column with methylene chloride:acetone (50:1; v:v) followed by elution with methylene chloride:acetone: isopropanol (100:10:2; v:v:v) yielded the desired product as a foamy oil; $1_H$ nmr ($CDCl_3$) δ 0.83 (3H, d, J=7 Hz), 0.88 (9H, s) 4.10 (H, bs), 4.29 (H, m), 4.64 (2H, d, J=8 Hz), 4.67 (H, m).

(c) 6(R)-[2-[8(S)-Hydroxy-2(S)-methyl-6(S)-hydroxyiminomethyl-1,2,3,4,4a(S),5,6,7,8,8a(S) decahydronaphthyl-1(S)]ethyl]-4(R)-(tert-butyl-dimethylsilyloxy)-3,4,5,6-tetrahydro-2H-pyran-2 one (3c)

Compound 3b (288 mg, 0.616 mmol) was dissolved in isopropanol (15 ml) and heated at reflux for 2 hours. After cooling the reaction mixture was concentrated in vacuo to leave a residue which afforded the title compound as a gummy oil; $1_H$ nmr ($CDCl_3$) δ 0.86 (3H, d, J=7 Hz), 0.90 (9H, s) 2.33 (H, d, J=14 Hz), 2.78 (H, m), 4.11 (H, m), 4,32 (H, m), 4.66 (H, m), 7,50 (H, d, J=6 Hz).

(d) 6(R)-[2-[8-Hydroxy-2(S)-methyl-6(S)-formyl-1,2,3,4,4a (S),5,6,7,8,8a(S)-decahydronaphthyl-1(S)]-ethyl]-4(R)-(tert-butyldimethylsilyloxy)-3,4,5,6-tetrahydro-2H-pyran-2-one (3d)

Sodium nitrite (477 mg 6.83 mmol) was added at 0° C. in one portion to a stirred solution of compound 3c (324 mg 0.683 mmol) in acetic acid (14 ml) and water (7 ml). The resulting mixture was stirred at 0° C. for 10 minutes, warmed to room temperature and stirred for 2.5 hours. The mixture was then diluted with water and extracted with diethyl ether. This ethereal extract was washed with water, 5% $NaHCO_3$ (twice), dried and filtered. Evaporation of the filtrate in vacuo afforded a brownish oily residue whose nmr spectrum is consistent with the structure for compound 2d; $1_H$ nmr $CDCl_3$) δ 0.80 (3H, d, J=7 Hz), 0.88 (9H, s), 4,30 (H, m) 4.55 (2H, m).

(e) 6(R)-[2-[8(S)-Hydroxy-2(S)-methyl-6(S)-hydroxymethyl-1,2,3,4,4a(S),5,6,7,8,8a(S)-decahydronaphthyl-1(S)]ethyl]-4(R)-(tert-butyldimethyl-silyloxy)-3,4,5,6-tetrahydro-2H-pyran-2-one (3e)

Powdered sodium borohydride (40 mg, 1.05 mmol) was added at 0° C. to a stirred solution of compound 3d (296 mg, 0.651 mmol) in 95% ethanol (15 ml) in one portion. The resulting mixture was stirred at 0° C. for 0.5 hours, then slowly treated with a solution of aqueous $(NH_4)_2SO_4$ (0.7 g in 15 ml of 2 $H_2O$). The resulting mixture was stirred at O° C. for 0.5 hours, diluted with water (60 ml) and extracted with diethyl ether. This extract was washed with water, 5% $NaHCO_3$, dried, filtered and evaporated to give a crude sample which was purified by flash chromatography. Elution of the column with methylene chloride:acetone:isopropanol (100:10:2; v:v:v) afforded the desired product as a white solid; mp 124°–7° C.; $1_H$ nmr ($CDCl_3$) δ 0.83 (3H, d, J=7 Hz), 0.90 (9H, s), 3.73 (H, d of d, J=11,6 Hz), 3.79 (H, d of d, J=11,6 Hz), 4.10 (H, bs) 4.31 (H, m), 4.70 (H, m).

Anal Calc'd for $C_{25}H_{46}O_5Si$ C, 66.03; H, 10.20. Found: C, 66.07; H, 10.38.

(f) 6(R)-[2-[8(S)-hydroxy-2(S)-methyl-6(S)-benzyloxymethoxymethyl-1,2,3,4,4a(S),5,6,7,8,8a(S)-decahydronaphthyl-1(S)]-ethyl]-4(R)-tert-butyldimethyl-silyloxy)-3,4,5,6-tetrahydro-2H-pyran-2-one (3f)

To a stirred solution of compound 3e (9.7 g, 21.3 mmol) and diisopropylethylamine (10 mL, 57.4 mmol) in $CH_2Cl_2$ (25 mL) cooled to 0° C. was added dropwise a solution of benzyl chloromethyl ether (3.76 g, 24 mmol) in $CH_2Cl_2$ (10 mL). The resulting mixture was stirred at 0° C. for 10 minutes, allowed to warm to room temperature, stirred at room temperature for 22 hours and then poured into ice water. The heterogeneous mixture was extracted with diethyl ether. The organic phase was separated, washed successively with dilute HCl, water, aqueous $NaHCO_3$ and water, dried ($Na_2SO_4$), filtered and evaporated in vacuo to afford a residue which was purified by flash chromatography on silica gel. Elution with $CH_2Cl_2$ acetone (50:1; v:v) removed the impurities. Continued elution with $CH_2Cl_2$ acetone (20:1; V:V) provided the title compound as a viscous oil; $1_H$ nmr ($CDCl_3$) δ 0.82 (3H, d, J=7 Hz), 0.88 (9H, s), 2.6 (2H, m), 2.70 (H, d, J=6 Hz), 3.75 (2H, m), 4.0 (H, m), 4.28 (H, m), 4.60 (H, d, J=12 Hz), 4.62 (H, d, J=12 Hz), 4.66 (H, m), 4.78 (H, d, J=6 Hz), 4.81 (H, d, J=6 Hz), 7.3 (5H, m).

(g) 6(R)-[2-[8(S)-(2,2-Dimethylbutyryloxy)-2(S)-methyl-6(S)-benzyloxymethoxymethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (3g)

Powdered lithium bromide (6.4 g, 74 mmol) was added under $N_2$ to a stirred mixture of 2,2-dimethylbutyryl chloride (4.97 g, 37 mmol) in pyridine (100 mL) and the resulting mixture was stirred and warmed to 40° C. until a clear solution was obtained. To the resulting solution was added 4-dimethylaminopyridine (0.3 g, 2.45 mmol) and a solution of 3f (7.25 g, 13 mmol) in pyridine (30 mL). The resulting mixture was stirred and heated at 90° C. for 3.5 hours, cooled to room temperature, poured into ice water and extracted with diethyl ether. The organic phase was separated, washed with dilute HCl, aqueous $NaHCO_3$ and saturated brine, dried ($Na_2SO_4$), filtered and evaporated in vacuo to give an oily residue which was purified by flash chromatography on silica gel. Elution with $CH_2Cl_2$-acetone (50:1; v:v) afforded the title compound as a viscous oil; $1_H$ nmr ($CDCl_3$) δ 0.82 (3H, d, J=7HZ), 0.83 (3H, t, J=7 Hz), 0 88 (9H, s), 1.14 (3H, s), 1.15 (3H, s), 2.67 (2H, m), 3.39 (H, d of d, J=10, 6 Hz), 3.86 (H, t, J=10 Hz), 4.27 (H, m), 4.54 (H, d, J=16 Hz), 4.61 (H, d, J=16 Hz), 4.74 (2H, s), 5.13 (H, m), 7.32 (5H, m).

(h) 6(R)-[2-[8(S)-(2,2-Dimethylbutyryloxy)-2(S)-methyl-6-(S)-hydroxymethyl-1,2,3,4,4a(S),5,6,7,8,8a (S)-decahydronaphthyl-(S)]ethyl]-4(R)-(tert-butyldimethylsilyloxy)-3,4,5,6-tetrahydro-2H-pyran-2-one (3h)

A mixture of compound 3g (6.1 g, 8.85 mmol), 10% Pd/C (0.5 g) and acetic acid (3 drops) in isopropanol (200 mL) was hydrogenated in a Paar apparatus for 4 hours. The resulting mixture was treated with powdered $NaHCO_3$ (1 g), stirred for 15 minutes and filtered. The filtrate was evaporated in vacuo to provide a residue which was dissolved in toluene (100 mL). The resulting solution was evaporated in vacuo to provide a residue which again was dissolved in toluene (100 mL). Evaporation of this solution in vacuo gave a residue which crystallized from diethyl ether hexane to provide the title compound as a colorless solid, mp 70°–71° C.; 'H nmr ($CDCl_3$) δ 0.82 (3H, d, J=7 Hz), 0.83 (3H, t, J=7 Hz), 0.87 (9H, s), 1.15 (3H, s), 1.16 (3H, s), 2.66 (2H, m), 3.55 (H, m), 3.78 (H, m), 4.28 (H, m), 4.65 (H, m), 5.14 (H, m).

Anal. Cal'd for C31H56O6Si: C, 67.34; H, 10.21. Found: C, 67.21; H, 10.35.

6(R)-[2-[(S)-(2,2-Dimethylbutyryloxy)-2(S)-methyl-6(S)-formyl-1,2,3,4,4a(S),5,6,7,8,8a(S)-decahydronaphthyl-1(S)]-ethyl]-4(R)-(tert-butyldimethylsilyloxy)-3,4,5,6-tetrahydro-2H-pyran-2-one (3i)

To a stirred solution of oxalyl chloride (152 mg, 1.2 mmol) in $CH_2Cl_2$ (10 mL) cooled at −78° C. was added dimethylsulfoxide 156 mg, 2 mmol) via syringe under $N_2$. The resulting mixture was stirred at −78° C. for 15 minutes and treated with a solution of compound 3h (383 mg, 0.693 mmol) in $CH_2Cl_2$ (5 mL) added dropwise. The resulting mixture was stirred at −78° C., for 30 minutes, treated with triethylamine (253 mg, 2.5 mmol), stirred for an additional 10 minutes at −78° C. warmed to room temperature, poured into ice water and extracted with diethyl ether. The organic extract was washed with aqueous $NaHCO_3$ and water, dried ($Na_2SO_4$), filtered and evaporated in vacuo to provide the title compound as a pale yellow oil; $1_H$ nmr ($CDCl_3$) δ 0.83 (3H, d, J=7 Hz), 0.83 (3H, t, J=7 Hz), 0.89 (9H, s), 1.10 (3H, s), 1.12 (3H, s), 2.58 (2H, m), 4.28 (H, m), 4.55 (H, m), 5.20 (H, m), 9.63 (H, s).

(j) 6(R)-[2-[8(S)-(2,2-Dimethylbutyryloxy)-2(S)-methyl-6(S)-(1-hydroxyethyl)-1,2,3,4,4a(S),5,6,7,8,8a(S)-decahydronaphthyl-1(S)]-ethyl]-4(R)-(tert-butyldimethylsilyloxy)-3,4,5,6-tetrahydro-2H-pyran-2-one (3j)

A solution of methylmagnesium bromide (3.0M in diethyl ether, 0.50 mL, 1.5 mmol) was added dropwise to a stirred solution of compound 3i (700 mg, 1.27 mmol) dissolved in dry diethyl ether (20 mL) at −78° C. under an argon atmosphere. The cooling bath was removed and the reaction mixture was stirred with gradual warming to room temperature over about a 2 hour period before quenching with a saturated brine solution (10 mL). The reaction mixture was distributed between diethyl ether (100 mL) and water (50 mL). The diethyl ether layer was separated, dried, filtered and evaporated to leave crude product which was purified by flash chromatography on a silica gel column. Elution of the column with chloroform:acetone (40:1/v:v) gave the two diastereomeric alcohols as clear colorless glasses.

Isomer A: $R_f$=0.17, diagnostic nmr peaks ($CDCl_3$) δ 4.02 (H, m), 4.27 (H, m), 4.54 (H, m), 5.12 (H, m).

Isomer B: $R_f$=0.07, diagnostic nmr peaks ($CDCl_3$) δ 3.98 (H, m), 4.27 (H, m), 4.56 (H, m), 5.16 (H, m).

(k) 6(R)-[2-[8(S)-(2,2-dimethylbutyryloxy)-2(S)-methyl-6(S)-(1 hydroxyethyl)-1,2,3,4,4a,(S),5,6,7,8,8a(R)-decahydronaphthyl-1(S)]ethyl]-4(R)-hydroxy-3,4,5,6-tetrahydro-2H-pyran-2-one (Isomer A)

n-Tetrabutylammonium fluoride solution (1M in THF, 1.65 mL, 1.65 mmol) was added to a stirred solution of compound 3j isomer A (180 mg, 310 μmol) and acetic acid (180 μL) in tetrahydrofuran (3 mL). The resulting solution was stirred at room temperature for 18 hours. Thin layer chromatography now showed only a trace of silyl ether and was thus diluted with water (30 mL) and the crude product was extracted into diethyl ether (100 mL). The etherial extract was washed with 0.1N hydrochloric acid (100 mL), water (2×50 mL), saturated sodium bicarbonate solution (50 mL), dried, filtered, and evaporated to yield the crude alcohol which was purified by flash chromatography on silica gel. Elution of the column with methylene chloride:acetone (6:1/v:v) gave the desired diol as a clear colorless glass: $R_f$=0.46 chloroform:acetone (4:1/v:v), diagnostic nmr peaks ($CDCl_3$) 6 2.6 (H, md, J=18 Hz), 2.73 (H, dd, J=5, 18 Hz), 4.03 (H, m), 4.35 (H,m), 4.56 (H,m), 5.15 (H,m).

Anal Calc'd for $C_{26}H_{44}O_6$: C, 68,99; H, 9.80. Found: C, 69.07; H, 9.82.

(l) 6(R)-[2-[8(S)-(2,2-dimethylbutyryloxy)-2(S)-methyl-6(S)-(1-hydroxyethyl)-1,2,3,4,4a,(S),5,6,7,8,8a(R)-decahydronaphthyl-1(S)]ethyl]-4(R)-hydroxy-3,4,5,6-tetrahydro-2H-pyran 2-one (Isomer B)

Aqueous hydrofluoric acid (49%, 0.42 mL) was added dropwise to a stirred solution of compound 3j isomer B (200 mg, 0.34 mmol) in acetonitrile (8 mL) at about 10° C. The cooling bath was removed and the clear colorless solution was stirred at room temperature for 1¼ hour. The reaction mixture was distributed between diethyl ether (100 mL) and saturated sodium bicarbonate solution (50 mL). The ethereal layer was dried, filtered, and evaporated to provide crude diol which was purified by flash chromatography on silica gel. Elution of the column with methylene chloride:acetone (6:1/v:v) gave the desired diol as a clear colorless glass: $R_f$=0.31 chloroform:acetone (4:1/v:v), diagnostic nmr peaks ($CDCl_3$) δ 2.6 (H, md, J=18 Hz), 2.73 (H, dd, J=5,18 Hz), 3.98 (H, m), 4.14 (H, m), 4.56 (H,m), 5.18 (H, m). MS (FAB)m/z 453 ($MH^+$).

Anal Calc'd for $C_{26}H_{44}O_6$: C, 68.99; H, 9.80. Found: C, 68.96; H, 10.04.

EXAMPLE 4

(j) 6(R)-[2-[8(S)-(2,2-Dimethylbutyryloxy)-2(S)-methyl-6(S)-(α-hydroxybenzyl)-1,2,3,4,4a(S),5,6,7,8,8a(S)-decahydronaphthyl-1(S)]ethyl]-4(R)-(tert butyldimethylsilyloxy)-3,4,5,6-tetrahydro-2H-pyran 2 one (4j)

Utilizing the general method described in Example 3 step j except that the methylmagnesium bromide was replaced by phenylmagnesium chloride the above titled compound was obtained as a single diastereomer.

(k) 6(R) [2-[8(S)-(2,2-Dimethylbutyryloxy)-2(S)-methyl-6(S)-(α-hydroxybenzyl-1,2,3,4,4a(S),5,6,7,8,8a-(S)-decahydronaphthyl-1(S)]ethyl]-4(R) hydroxy-3,4,5,6 tetrahydro-2H-pyran 2 one (4k)

Utilizing the general method described in Example 3 step 1 except that 1; isomer A was replaced by 4j, the above titled compound was obtained as a colorless solid following recrystallization from acetonitrile water, mp 196°–196.5° C., diagnostic nmr peaks ($CDCl_3$) δ 2.64 (H, md, J=18 Hz), 2.74 (H, dd, J=5, 18 Hz), 4.35 (H, m) 4.59 (H, m), 4.88 (H, dd, J=3, 10.8 Hz), 5.29 (H, d, J=3 Hz).

Anal. Calc'd for $C_{31}H_{46}O_6$: C, 72.34; H, 9.01 Found: C, 72.29; H, 9.29.

EXAMPLE 5

Preparation of 6(R)-[2-[8(S)-(Cyclohexylcarbonyloxy)-6(S)-hydroxymethyl-2(S)-methyl-1,2,3,4,4a(S),5,6,7,8,8a(S)-decahydronaphthyl-1(S)]ethyl]-4(R)-hydroxy-3,4,5,6-tetrahydro-2H-pyran-2-one (a) 6(R)-[2-[8(S)-Cyclohexylcarbonyloxy)-6(S)-(tert-butyldiphenylsilyloxymethyl)-2(S)-methyl-1,2,3,4,4a(S),5,6,7,8,8a(S)-decahydronaphthyl-1(S)]ethyl]-4(R)-(tert butyldimethylsilyloxy)-3,4,5,6-tetrahydro-2H-pyran-2-one (5a)

A solution of cyclohexylcarbonyl chloride (73 mg, 0.5 mmol) in pyridine (2 ml) was added to a stirred mixture of 6(R)-[2-[8(S)-hydroxy-2(S)-methyl-6(S)-(tert-butyldiphenylsilyloxymethyl)-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (116 mg, 0.167 mmol), the compound 2f, and 4 (dimethylamino) pyridine (24 mg, 0.2 mmol) in pyridine (2 ml). The resulting mixture was stirred at room temperature under $N_2$ for 3 hours and then heated at 65° C. for 1.5 hours. After cooling, the reaction mixture was poured into cold water and extracted with diethyl ether. The ethereal extract was washed successively with dilute hydrochloric acid, water and 5% $NaHCO_3$. After drying, it was filtered and evaporated in vacuo to leave a residue which was purified by flash chromatography. Elution of the column with methylene chloride:acetone (100:1; V:V) yielded the desired compound as a colorless gummy oil; $1_H$ nmr ($CDCl_3$) δ 0.83 (3H, d, J=7 Hz), 0.90 (9H, s), 1.08 (9H, s), 3.54 (H, d of d, J=11, 6 Hz), 3.83 (H, t, J=11 Hz), 4.28 (H, m), 4.56 (H, m), 5.04 (H, m), 7.32 7.5 (6H, m), 7.6 7.8 (4H, m).

(b) 6(R)-[2-[8(S)-(Cyclohexylcarbonyloxy) 6(S)-hydroxymethyl-2(S)-methyl-1,2,3,4,4a(S),5,6,7,8,8a(S)-decahydronaphthyl-1(S)]ethyl]-4(R)-hydroxy-3,4,5,6-tetrahydro-2H-pyran-2 one (5b)

By following the general procedure of Example 2, Step (h), but using compound 5a in place of compound 2h, there was obtained the desired product as a colorless, gummy oil; $1_H$ nmr ($CDCl_3$) δ 0.86 (3H, d, J=7 Hz), 2.30 (H, m), 2.63 (H, m of d, J=18 Hz), 2.76 (H of d, J=18, 5 Hz), 3 58 (H, d of d, J=11, 6 Hz), 3.81 (H, t, J=11 Hz), 4 37 (H, m), 4.60 (H, m), 5.18 (H, m).

Anal Calc'd for $C_{26}H_{42}O_6 \cdot 0.4H_2O$: C, 68.21; H, 9.42. Found: C, 68.15; H, 9.53.

EXAMPLE 6

Preparation of 6(R)-[2-[8(S)-(2,2-Dimethylbutyryloxy)-6(R)-hydroxymethyl-2(S) methyl-1,2,3,4,6,7,8,8a(R)-octahydronaphthyl-1(S)] ethyl]-4(R)-hydroxy-3,4,5,6-tetrahydro-2H-pyran-2-one (a) 6(R)-[2-[8(S)-Hydroxy-2(S),6(R)-dimethyl-1,2,3,4,6,7,8,8a(R)-octahydronaphthyl-1(S)]ethyl]-4(R)-(tert-butyldimethylsilyloxy)-3,4,5,6-tetrahydro-2H-pyran-2-one A solution (200 ml) of 50% toluene in absolute ethanol was deoxygenated by bubbling $N_2$ through it for 15 minutes. Wilkinson's catalyst (2 g) was added to the solution and the mixture reduced on the Paar hydrogenation apparatus at 50 psi $H_2$ for 90 minutes. 6(R)-[2-[8(S)-Hydroxy-2(S),6(R)-dimethyl-1,2,6,7,8,8a-(R)-hexahydronaphthyl-1(S)]ethyl]-4(R)-(tert-butyldimethylsilyloxy)-3,4,5,6-tetrahydro-2H-pyran-2-one (4.0 g, 9.0 mmol.) was added and the solution hydrogenated at 58 psi $H_2$ for two days. The solvent was removed in vacuo and the residue stirred with diethyl ether (500 ml) for 15 minutes and then filtered. The filtrate was evaporated in vacuo to give a brown solid which was dissolved in toluene (200 ml) containing thiourea (2.6 The mixture was heated at 80° C. for 2 hours and then cooled to 0° C. and filtered. The filtrate was evaporated in vacuo and the solid residue chromatographed on a 7×18 cm column of silica gel. The column was eluted with 20% ethyl acetate in hexane and 25 ml fractions were collected. Fractions 54–90 were combined and evaporated in vacuo to yield the title compound as a colorless solid. Crystallization of the solid from aqueous $CH_3CN$ provided an analytical sample as colorless needles, mp 145°–6° C.; $1_H$ nmr ($CDCl_3$) δ 0.070 (3H, s), 0.077 (3H, s), 0.88 (9H, s), 0.90 (3H, d, J=7 Hz), 1,17 (3H, d, J =7 Hz), 2,58 (2H, m), 4,16 (H, m), 4.28 (H, m), 4.66 (H, m), 5.41 (H, m).

Anal Calc'd for $C_{25}H_{44}O_{45}$: C, 68.76, H, 10.50. Found: C, 68.72; H, 10.32.

(b) 6(R)-[2-[8(S)-(2,2-Dimethylbutyryloxy)-6(R)-hydroxymethyl-2(S)-methyl-1,2,3,4,6,7,8,8a(R)-octahydronaphthyl-1(S)]ethyl]-4(R)-hydroxy-3,4,5,6-tetrahydro-2H-pyran-2-one By substituting an equimolar amount of the title compound in Step (a) of this example for 6(R)-[2-[8(S)-hydroxy-2(S),6(S)-dimethyl-1,2,3,4,4a-5,6,7,8,8a(S)-decahydronaphthyl-1(S)]ethyl]-4(R)-(tert-butyldimethylsilyloxy)-3,4,5,6-tetrahydro-2H-pyran-2-one in Step (a) of Example 2 and then following the general procedures of Steps (a) through (h) of Example 2, there was obtained a corresponding amount of the title compound as an amorphorus solid; $1_H$ nmr ($CDCl_3$) δ 0.85 (3H, t, J=Hz), 0.90 (3H, d, J=7 Hz), 1,14 3H, s), 1,16 (3H, s), 3.54 (H, m), 3.65 (H, m), 4.37 (H, m), 4.59 (H, m), 5.35 (H, m), 5.47 (H, m).

Anal Calc'd for $C_{25}H_{40}O_6 \cdot 0.5H_2O$: C, 67.38; H, 9.57. Found: C, 67.66; H, 9.28.

EXAMPLE 7

Preparation of 6(R)-[2-[8(S)-(2,2-Dimethylbutyryloxy)-2(S)-methyl-6(S)-carboxy-1,2,3,4,4a(S),5,6,7,8,8a(S)-decahydronaphthyl-1(S)] ethyl]4(R)-hydroxy 3,4,5,6-tetrahydro-2H-pyran-2-one (a)

6(R)-[2-[8(S)-2,2-Dimethylbutryloyxy)-2(S)-methyl-6(S)-formyl-1,2,3,4,4a(S),5,6,7,8,8a(S)-decahydronaphthyl-1(S)]ethyl]-4(R)-hydroxy 3,4,5,6-tetrahydro-2H-pyran 2-one (7a)

A mixture of compound 2h (100 mg, 0.228 mmol), tris(triphenylphosphine) ruthenium (II) chloride (120 mg, 0.125 mmol) and sodium carbonate (40 mg) in benzene (7 ml) and methylene chloride (2 ml) was stirred at ambient temperature under $N_2$ for 24 hours. The reaction mixture was diluted with diethyl ether (10 ml) and filtered through diatomaceous earth and silica gel which was subsequently washed with methylene chloride. The combined filtrate and washings were concentrated in vacuo to yield a crude residue. The residue was purified by flash chromatography on silica gel eluted with methylene chloride:acetone:isopropanol (100:10:2; V:V:V) to afford the desired product as a gummy oil; $1_H$ nmr ($CDCl_3$) δ 0.82 (3H, d, J=7 Hz), 0.83 (3H, t, J=7 Hz), 1.10 (3H,s), 1.12 (3H,s), 2.60 (H, m of d, J=18 Hz), 2.73 (H, d of d, J=18,5 Hz), 4.37 (H,m), 4.57 (H,m), 5.23 (H,m), 9.64 (H, s)

(b) 6(R)-[2-[8(S)-(2,2-Dimethylbutyryloxy)-2(S)-methyl-6(S)-carboxy-1,2,3,4,4a(S)5,6,7,8,8a(S)-decahydronaphthyl-1(S)]ethyl]4(R)-hydroxy 3,4,5,6-tetrahydro-2H-pyran-2-one (7b)

To a stirred mixture of compound 7a (14 mg, 0.032 mmol) and sulfamic acid (4.4 mg, 0.045 mmol) in THF (1.5 ml) and water (0.5 ml) was added solid sodium chlorite (80% active, 5.6 mg, 0.05 mmol). The reaction mixture was stirred at ambient temperature for 45 minutes, poured into cold water (15 ml) and extracted with diethyl ether and methylene chloride. The organic phase was separated, dried ($MgSO_4$) filtered and evaporated in vacuo to give a crude residue. The residue was purified by flash chromatography on silica gel eluted with methylene chloride:acetone:isopropanol (100:10:5; v:v:v) to afford the desired product as a gummy oil; $1_H$ nmr ($CDCl_3$) δ 0.83 (3H, d, J=7 Hz), 0.83 (3H, t, J=7 Hz), 1.08 (3H, s), 1.09 (3H, s), 2.14 (H, m of d, J=13 Hz), 2.73 (H, d of d, J=18,5 Hz), 4.36 (H, m), 4.57 (H, m), 5.19 (H, m).

EXAMPLE 8

Preparation of 6(R)-[2-[8(S)-(2,2-Dimethylbutyryloxy)-2(S)-methyl-6(S)-methoxycarbonyl-1,2,3,4,4a(S)5,6,7,8,8a(S)-decahydronaphthyl-1(S)]ethyl]4(R)-hydroxy-3,4,5,6-tetrahydro-2H-pyran-2-one To a solution of compound 7b (9.6 mg, 0.021 mmol) in isopropanol (2 ml) at ambient temperature was added a solution of trimethylsilyl-diazomethane 10% in hexane, 0.3 ml. The reaction mixture was stirred at ambient temperature for 18 hours and then concentrated in vacuo to give a crude residue. The residue was purified by flash chromatography on silica gel eluted with methylene chloride:acetone:isopropanol 100:10:2; v:v:v) to afford the desired product as a gummy oil; $1_H$ nmr ($CDCl_3$) δ 0.83 (3H, d, J=7 Hz), 0.83 (3H, t, J=7 Hz), 1.09 (3H, s), 1.12 (3H,3), 1.52 (2H, t, J=7 Hz), 2.16 (H, m of d, J=13 Hz), 2.60 (H, m of d, J=18 Hz), 2.74 (H, d of d, J=18,5 Hz), 3.66 (3H,s), 4.37 (H, m), 4.57 (H, m), 5.18 (H, m).

EXAMPLE 9

Preparation of 6(R)-[2-[8(S)-(2,2-Dimethylbutyryloxy)-6(R)-(2,2-dimethylbutyryloxymethyl)-2(S)-methyl-1,2,3,4,6,7,8,8a(R)-octahydronaphthyl-1(S)]-ethyl]-4(R)-hydroxy-3,4,5,6-tetrahydro-2H-pyran-2-one To a solution of tetra-n-butylammonium fluoride (211 μl, 1M in tetrahydrofuran, 0.21 mmol), acetic acid (17 mg, 0.28 mmol) and tetrahydrofuran (5 ml) was added 6(R)-[2-[8(S)-(2,2-dimethylbutyryloxy)-6(R)-(2,2-dimethylbutyryloxymethyl)-2(S)-methyl-1,2,3,4,6,7,8,8a(R)-octahydronaphthyl-1(S)]-ethyl]-4(R)-(tert-butyldimethylsilyloxy)-3,4,5,6-tetra-hydro-2H-pyran-2-one which was isolated from the reaction of 2,2-dimethylbutyryl chloride and 6(R)-2-[8(S)-hydroxy-6(R)-(tert-butyldimethylsilyloxymethyl)-2(S)-methyl-1,2,3,4,6,7,8,8a(R)-octahydronaphthyl-1(S)]ethyl]4(R)-(tert-butyldimethylsilyloxy)-2,3,5,6-tetra-hydro-2H-pyran-2-one according to the general procedure of Example 2, Step (g). The reaction mixture was stirred at ambient temperature for 18 hours and then evaporated in vacuo to give a crude residue. The residue was partitioned between diethyl ether (50 ml) and water (10 ml). The aqueous phase was washed with diethyl ether (2×50 ml). The combined organic phase and the washings were washed with saturated sodium bicarbonate (5 ml) and brine (2×25 ml), dried ($MgSO_4$) and evaporated in vacuo to yield a gummy residue. The residue was purified by flash chromatography on silica gel eluted with 10 percent acetone in methylene chloride (150 ml) and then 20 percent acetone in methylene chloride to afford the desired product. This product was further purified by preparative high pressure liquid chromatography and after trituration with hexane gave a crystalline product; mp 119°–121° C.; $1_H$ nmr ($CDCl_3$) δ 0.84 (6H, m), 0.90 (3H, d, J=7 Hz), 1.14 (12H, s), 3,83 ($1_H$ d of d, J=10,9 Hz), 4.19 (H, d of d, J=10,9 Hz), 4.37 (H, m), 4.59 (H, m), 5.36 (H, m), 5.40 (H, m), FAB MS 535 (M+H), 557 (M+Na).

EXAMPLE 10

Preparation of 6(R)-[2-[8(S)-(2,2-Dimethylbutyryloxy)-6(S)-hydroxymethyl-2(S)-methyl-1,2,6,7,8,8a(R)-hexahydronaphthyl-1(S)]ethyl]-4(R)-hydroxy-3,4,5,6-tetrahydro-2H-pyran-2-one To a stirred solution of 6(R)-[2-[8(S)-(2,2-dimethylbutylbutyryloxy)-6(S)-carboxy-2(S)-methyl-1,2,6,7,8,8a(R)-hexahydronaphthyl-1(S)]ethyl]-4(R)-hydroxy-3,4,5,6-tetrahydro 2H-pyran 2-one (102 mg, 0.23 mmol) in 4 Å sieve-dried $CH_2Cl_2$ (2.3 mL) was added triethylamine (32 μl, 0.23 mmol). The resulting mixture was cooled to −70° C. and isobutyl chloroformate (30 μl, 0.23 mmol) was added over a 30-second period with stirring. After stirring for 30 minutes at −70° C., the mixture was allowed to warm to 0° C. over a 20 minute period. The resulting solution was added over a 30 second period to a freshly prepared solution of $NaBH_4$ (8.8 mg, 0.23 mmol) in EtOH (2 ml) with stirring at 0° C. After 10 minutes, the cold mixture was partitioned between EtOAc (20 mL) and 0.1N HCl. The organic phase was separated, washed with water (2×5 mL) and saturated brine (5 mL), dried ($Na_2SO_4$), filtered and evaporated viscous oil (95 mg). Chromatography of this oil on silica gel using 0 10% $CH_{30}H$ in $CHCl_3$ as eluant afforded the title compound which was identical by comparative tlc and $1_H$ nmr spectral analysis to an authentic sample isolated from a microbiological fermentation broth of the sodium salt of 7-[1,2,6,7,8,8a(R)-hexahydro-2(S),6(R)-dimethyl-8(S)-(2,2-dimethylbutyryloxy)-1(S)naphthyl]-3(R),5(R)-dihydroxyheptanoic acid.

EXAMPLE 11

Preparation of 6(R)-[2-[8(S)-(2,2-Dimethylbutyryloxy)-6(R)-hydroxymethyl-2(S)-methyl-1,2,6,7,8,8a(R)-hexahydronaphthyl-1(S)]ethyl]-4(R)-hydroxy-3,4,5,6-tetrahydro-2H-pyran-2-one By substituting an equimolar amount of the 6(R)-carboxylic acid for the 6(S)-carboxylic acid used in Example 10 and using the procedure described therein, there was obtained a corresponding amount of the title compound.

EXAMPLE 12

Preparation of 6(R)-[2-[8(S)-(2,2-Dimethylbutyryloxy)-6(S)-(N,N-dimethyl) aminocarbonyl-2(S)methyl-1,2,6,7,8,8a(R)-hexahydronaphthyl-1(S)]ethyl]-4(R)-hydroxy-3,4,5,6-tetrahydro 2H-pyran 2-one To a stirred solution of 6(R)-[2-[8(S)-(2,2-dimethylbutyryloxy) 6(S)-carboxy-2(S)-methyl-1,2,6,7,8,8a (R)-hexahydronaphthyl-1(S)]ethyl]-4(R)-hydroxy-3,4,5,6-tetrahydro-2H-pyran-2-one (100 mg) in $CH_2Cl_2$ (1 mL) cooled to 0° C. and maintained under $N_2$ was added dropwise a solution of carbonyl diimidazole (39 mg) in $CH_2Cl_2$ (1 mL). After stirring for 1 hour at 0° C., the mixture was treated with dimethylamine hydrochloride (20 mg) and stirred for an additional 30 minutes. Then the mixture was partitioned between EtOAc and 1N HCl. The organic phase was separated, washed with aqueous $NaHCO_3$ and saturated brine, dried ($Na_2SO_4$), filtered and evaporated in vacuo to afford a residual oil. Chromatography of this oil on silica gel using a gradient of 1 5% $CH_{30}H$ in $CH_2Cl_2$ as eluant afforded the title compound as a solid, mp 148°–160° C. after recrystallation from EtOAc-hexane.

Anal. Calc'd for $C_{27}H_{41}N)_6$: C, 68.18; H, 8.69; N, 2.94. Found: C, 67.95; H, 8.97; N, 3.06.

EXAMPLE 13

Preparation of 6(R)-[2-[8(S)-(2,2-dimethylbutyryloxy)-6(S)-(N,N-diethyl) aminocarbonyl-2(S)-methyl-1,2,6,7,8,8a(R)-hexahydronaphthyl-1(S)]ethyl]-4(R)-hydroxy-3,4,5,6-tetrahydro-2H-pyran-2-one To a stirred solution of 6(R)-[2-[8(S)-(2,2-dimethylbutyryloxy)-6(S)-carboxy-2(S)-methyl-1,2,6,7,8,8a(R)-hexahydronaphthyl-1(S)]ethyl]-4(R)-hydroxy-3,4,5,6-tetrahydro-2H-pyran-2-one To a stirred solution of 6(R)-[2-[8(S)-(2,2-dimethylbutyryloxy)-6(S)-carboxy-2(S)-methyl-1,2,6,7,8,8a(R)-hexahydronaphthyl-1(S)]ethyl]-4(R)-hydroxy-3,4,5,6-tetrahydro-2H-pyran-2-one (100 mg) in $CH_2Cl_2$ (1.5 mL) cooled to 0° C. and maintained under $N_2$ was added triethylamine (31.3 ml ). After 15 minutes, isobutyl chloroformate (29.4 ml) was added and, after an additional 15 minutes, diethylamine (23.7 ml) was added. The resulting mixture was stirred at 0° C. for 30 minutes and then washed with 1N HCl followed by aqueous $NaHCO_3$. The organic phase was separated, dried ($Na_2SO_4$), filtered and evaporated in vacuo to afford a residual oil. Chromatography of this oil on silica gel using a gradient of 1–5% $CH_{30}H$ in $CH_2Cl_2$ as eluant afforded the title compound as a solid, mp 154°–155° C. after recrystallization from EtOAc hexane.

Anal. Calc'd for $C_{29}H_{45}NO_6$: C, 69.15; H, 9.01; N, 2.78. Found: C, 68.85; H, 9.09; N, 2.63.

EXAMPLE 14

Preparation of 6(R)-[2-[8(S)-(2,2-Dimethylbutyryloxy)-6(S)-propylaminocarbonyl-2 (S)-methyl-1,2,6,7,8,8a(R)-hexahydronaphthyl-1(S)] ethyl]-4(R)-hydroxy-3,4,5,6-tetrahydro-2H-pyran-2-one By substituting an equimolar amount of n-propylamine for the diethylamine used in Example 13 and using the procedure described therein, there was obtained the title compound as a colorless solid, mp 96°–105° C.

EXAMPLE 15

Preparation of 6(R)-[2-[8(S)-(2,2-Dimethylbutyryloxy)-6(S)-benzylaminocarbonyl-2 (S)-methyl-1,2,6,7,8,8a(R)-hexahydronaphthyl-1(S)] ethyl]-4(R)-hydroxy-3,4,5,6-tetrahydro-2H-pyran-2-one By substituting an equimolar amount of benzylamine for the diethylamine used in Example 13 and using the procedure described therein, there was obtained the title compound as a viscous oil.

EXAMPLE 16

Preparation of 6(R)-[2-[8(S)-(2,2-Dimethylbutyryloxy)-6(S)-(2-hydroxyethyl) aminocarbonyl-2(S)-methyl-1,2,6,7,8,8a(R)-hexahydronaphthyl-1(S)]ethyl]-4(R)-hydroxy-3,4,5,6-tetrahydro-2H-pyran-2-one By substituting an equimolar amount of 2-hydroxyethylamine for the diethylamine used in Example 13 and using the procedure described therein, there was obtained the title compound as a viscous oil.

EXAMPLE 17

Preparation of 6(R)-[2-[8(S)-(2,2-Dimethylbutyryloxy)-6(S)-phenylaminocarbonyloxymethyl-2(S)-methyl-1,2,6,7,8,8a(R)-hexahydronaphthyl (S)]ethyl]-4(R)-hydroxy-3,4,5,6-tetrahydro-2H-pyran-2-one To a stirred solution of 6(R)-[2-[8(S)-(2,2-dimethylbutyryloxy) 6(S)-hydroxymethyl-2(S)-methyl-1,2,6,7,8,8a(R)-hexahydronaphthyl-1(S)]ethyl]-4(R)-hydroxy-3,4,5,6-tetrahydro-2H-pyran-2-one (80 mg, 0.184 mmol) in sieve dried pyridine (3 mL) was added phenyl isocyanate (22 mg, 0.184 mmol). The resulting solution was stirred at room temperature for 72 hours and then was evaporated in vacuo to provide an oily residue. The residue was partitioned between $CHCl_3$ (125 mL) and 0.1N HCl (25 mL). The organic phase was separated, washed with 0.1N HCl (2×25 ml) and saturated brine (25 mL), dried ($Na_2SO_4$), filtered and evaporated in vacuo to give crude product. Chromatography of the crude product on silica gel using $CHCl_3$-$CH_{30}H$ (98:2, v:v) as eluant afforded the title compound as a colorless gum which solidified upon trituration with hexane, mp 115°–119° C.

Anal. Calc'd for $C_{32}H_{43}NO_7$: C,69.41; H, 7.83; N, 2.53. Found: C,69.51; H, 7.95; N, 2.67.

EXAMPLE 18

Preparation of 6(R)-[2-[8(S)-(2,2-Dimethylbutyryloxy)-2(S)-methyl-6(S)-(N,N-dimethyl)aminocarbonyl-1,2,3,4,4a(S),5,6,7,8,8a(S)-decahydronaphthyl-1(S)]ethyl]4(R)-hydroxy-3,4,5,6-tetrahydro-2H-pyran-2-one (a) 6(R)-[2-[8(S)-hydroxy-2(S-methyl-6(S)-benzyloxymethoxymethyl-1,2,3,4,4a(S),5,6,7,8,8a(S)-decahydronaphthyl-1(S)]-ethyl]-4(R)-tert-butyl-dimethylsilyloxy) 3,4,5,6-tetrahydro-2H-pyran-2-one (18a)

To a stirred solution of compound 2c (9.7 g, 21.3 mmol) and diisopropylethylamine (10 mL, 57.4 mmol) in $CH_2Cl_2$ (25 mL) cooled to 0° C. was added dropwise a solution of benzyl chloromethyl ether (3.76 g, 24 mmol) in $CH_2Cl_2$ (10 mL). The resulting mixture was stirred at 0° C. for 10 minutes, allowed to warm to room temperature, stirred at room temperature for 22 hours and then poured into ice water. The heterogeneous mixture was extracted with diethyl ether. The organic phase was separated, washed successively with dilute HCl, water, aqueous $NaHCO_3$ and water, dried ($Na_2SO_4$), filtered and evaporated in vacuo to afford a residue which was purified by flash chromatography on silica gel. Elution with $CH_2Cl_2$ acetone (50:1; v:v) removed the impurities. Continued elution with $CH_2Cl_2$ acetone (20:1: V:V) provided the title compound as a viscous oil; $1_H$ nmr ($CDCl_3$) δ 0.82 (3H, d, J=7 Hz), 0.88 (9H, s), 2.6 (2H, m), 2.70 (H, d, J=6 Hz), 3.75 (2H, m), 4.0 (H, m), 4.28 (H, m), 4.60 (H, d, J=12 Hz), 4.62 (H, d, J=12 Hz), 4.66 (H, m), 4.78 (H, d, J=6 Hz), 4.81 (H, d, J=6 Hz), 7.3 (5H, m).

(b) 6(R)-[2-[8(S)-(2,2-Dimethylbutyryloxy)-2(S)-methyl-6(S)-benzyloxymethoxymethyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (18b)

Powdered lithium bromide (6.4 g, 74 mmol) was added under $N_2$ to a stirred mixture of 2,2-dimethylbutyryl chloride (4.97 g, 37 mmol) in pyridine (100 mL) and the resulting mixture was stirred and warmed to 40° C. until a clear solution was obtained. To the resulting solution was added 4 dimethylaminopyridine (0.3 g, 2.45 mmol) and a solution of 18a (7.25 g, 13 mmol) in pyridine (30 mL). The resulting mixture was stirred and heated at 90° C. for 3.5 hours, cooled to room temperature, poured into ice water and extracted with diethyl ether. The organic phase was separated, washed with dilute HCl, aqueous $NaHCO_3$ and saturated brine, dried ($Na_2SO_4$), filtered and evaporated in vacuo to give an oily residue which was purified by flash chromatography on silica gel. Elution with $CH_2Cl_2$ acetone (50:1; v:v) afforded the title compound as a viscous oil; $1_H$ nmr ($CDCl_3$) δ 0.82 (3H, d, J=7 HZ), 0.83 (3H, t, J=7 Hz), 0.88 (9H, s), 1.14 (3H, s), 1.15 (3H, s), 2.67 (2H, m), 3.39 (H, d of d, J=10, 6 Hz), 3.86 (H, t, J=10 Hz), 4.27 (H, m), 4.54 (H, d, J=16 Hz), 4.61 (H, d, J=16 HZ), 4.74 (2H, S), 5.13 (H, m, 7.32 (5H, m).

(c) 6(R)-[2-[8(S)-(2,2-Dimethylbutyryloxy)-2(S)-methyl-6(S)-hydroxymethyl-1,2,3,4,4a(S),5,6,7,8,8a(S)-decahydronaphthyl (S)]ethyl]-4(R)-(tert-butyldimethylsilyloxy)-3,4,5,6-tetrahydro-2H-pyran-2-one (18c)

A mixture of compound 18b (6.1 g, 8.85 mmol), 10% Pd/C (0.5 g) and acetic acid (3 drops) in isopropanol (200 mL) was hydrogenated in a Paar apparatus for 4 hours. The resulting mixture was treated with powdered $NaHCO_3$ (1 g), stirred for 15 minutes and filtered. The filtrate was evaporated in vacuo to provide a residue which was dissolved in toluene (100 mL). The resulting solution was evaporated in vacuo to provide a residue which again was dissolved in toluene (100 mL). Evaporation of this solution in vacuo gave a residue which crystallized from diethyl ether-hexane to provide the title compound as a colorless solid, mp 70°–71° C.; 'H nmr ($CDCl_3$) δ 0.82 (3H, d, J=7 Hz), 0.83 (3H, t, J=7 Hz), 0.87 (9H, s), 1.15 (3H, s), 1.16 (3H, s), 2.66 (2H, m), 3.55 (H, m), 3.78 (H, m), 4.28 (H, m), 4.65 (H, m), 5.14 (H, m).

Anal. Cal'd for $C_{31}H_{56}O_6Si$: C, 67.34; H, 10.21. Found C, 67.21; H, 10.35.

(d) 6(R)-[2-[8(S)-(2,2-Dimethybutyryloxy)-2(S)-methyl-6(S)-formyl-1,2,3,4,4a(S),5,6,7,8,8a(S)-decahydronaphthyl-1(S)]-ethyl]-4(R)-(tert-butyldimethylsilyloxy) 3,4,5,6-tetrahydro-2H-pyran-one (18d)

To a stirred solution of oxalyl chloride (152 mg, 1.2 mmol) in $CH_2Cl_2$ (10 mL) cooled at −78° C. was added dimethylsulfoxide (156 mg, 2 mmol) via syringe under $N_2$. The resulting mixture was stirred at −78° C. for 15 minutes and treated with a solution of compound 18c (383 mg, 0.693 mmol) in $CH_2Cl_2$ (5 mL) added dropwise. The resulting mixture was stirred at −78° C., for 30 minutes, treated with triethylamine (253 mg, 2.5 mmol), stirred for an additional 10 minutes at −78° C. warmed to room temperature, poured into ice water and extracted with diethyl ether. The organic extract was washed with aqueous $NaHCO_3$ and water, dried ($Na_2SO_4$), filtered and evaporated in vacuo to provide the title compound as a pale yellow oil; $1_H$ nmr ($CDCl_3$) δ 0.83 (3H, d, J=7 Hz), 0.83 (3H, t, J=7 Hz), 0.89 (9H, s), 1.10 (3H, s), 1.12 (3H, s), 2.58 (2H, m), 4.28 (H, m), 4.55 (H, m), 5.20 (H, m), 9.63 (H, s).

(e) 6(R)-[2-[8(S)-(2,2-Dimethylbutyryloxy)-2(S)-methyl-6(S)-carboxy-1,2,3,4,4a(S),5,6,7,8,8a(S)-decahydronaphthyl-1(S)]ethyl]-4(R)-(tert-butyldimethylsilyloxy) 3,4,5,6-tetrahydro-2H-pyran-2-one (18e)

To a stirred mixture of compound 18d (380 mg, 0.69 mmol) and sulfamic acid (97 mg, 1 mmol) in THF water (5:1; v:v; 24 mL) cooled at 0° C. was added sodium chlorite (113 mg, 80% active, 1 mmol) in one portion. The resulting mixture was stirred at 0° C. for 10 minutes, warmed to room temperature and stirred for 2 hours. Then the mixture was poured into aqueous sodium thiosulfate and extracted with diethyl ether. The organic extract was washed with water, dried ($Na_2SO_4$), filtered and evaporated in vacuo to provide a residue which was purified by flash chromatography on silica gel. Elution with $CH_2Cl_2$ acetone (10:1; v:v) afforded the title compound as a colorless gum; $1_H$ nmr ($CDCl_3$) δ 0.83 (3H, t, J=7 Hz), 0.84 (3H, d, J=7 Hz), 0.89 (9H, s), 1.10 (3H, s), 1.12 (3H, s), 2.15 (H, d, J=9 Hz), 2.60 (2H, m), 2.68 (2H, m) 4.30 (H, m), 4.58 (H, m), 5.68 (H, m).

(f) 6(R)-[2-[8(S)-(2,2-Dimethylbutyryloxy)-2(S)-methyl-6(S)-chlorocarbonyl-1,2,3,4,4a(S),5,6,7,8,a(S)-decahydronaphthyl-1(S)]ethyl]-4(R)-(tert-butyldimethylsilyloxy) 3,4,5,6-tetrahydro-2H-pyran 2-one (18f)

DMF (1 drop) was added to a magnetically stirred solution of compound 18e (56 mg, 0.1 mmol) and oxalyl chloride (19 mL, 0.22 mmol) in benzene (2 mL) The resulting mixture was stirred at ambient temperature for 2 hours to provide a heterogeneous mixture which was decanted. Evaporation of the decantate in vacuo gave the title compound as a pale yellow oil; $1_H$ nmr ($CDCl_3$ δ 0.072 (3H, s), 0.082 (3H, s), 0.88 (9H, s), 1.13 (3H, s), 1.16 (3H, s), 3.02 (H, m), 4.28 (H, m), 4.55 (H, m), 5.20 (H, m).

(g) 6(R)-[2-[8(S)-2,2-Dimethylbutyryloxy)-2(S)-methyl-6(S)-(N,N dimethyl)aminocarbonyl-1,2,3,4,4a(S),5,6,7,8,8a(S)-decahydronaphthyl-1(S)]ethyl]-4(R)-(tert-butyl dimethylsilyloxy) 3,4,5,6-tetrahydro-2H pyran 2-one (18g)

Dimethylamine was bubbled slowly into a magnetically-stirred solution of compound 18f (58 mg, 0.1 mmol) in diethyl ether (10 mL) until the precipitation of dimethylammonium chloride ceased. Then the mixture was stirred at ambient temperature for 18 hours and filtered. Evaporation of the filtrate in vacuo provided a residual oil which was chromatographed on silica gel (230–400 mesh, 3×15 cm). Elution with isopropanol-hexane (1:5; v:v) afforded the title compound as a colorless oil; $1_H$ nmr ($CDCl_3$ δ 0.073 (3H, s), 0.084 (3H, s), 0.88 (9H, s), 1.09 (6H, s), 2.89 (3H, s), 2.95 (3H, s), 4.30 (H, m), 4.56 (H, m), 5.14 (H, m).

(h) 6(R)-[2-[8(S)-(2,2-Dimethylbutyryloxy)-2(S)-methyl-6(S)-(N,N dimethyl)aminocarbonyl-1,2,3,4,4a(S),5,6,7,8,8a(S) decahydronaphthyl-1(S)]-ethyl-4(R)-hydroxy-3,4,5,6-tetrahydro-2H-pyran-2-one (18h)

To a stirred solution of compound 18g (78 mg, 0.13 mmol) and acetic acid (30mL, 0.525 mmol) in THF (10 mL) was added tetra-n-butylammonium fluoride (1M in THF, 394 mL, 0.394 mmol. After stirring at ambient temperature for 18 hours, additional tetra-n-butylammonium fluoride (394 mL) and acetic acid (30 mL) were added to the mixture and stirring was continued for 24 hours. Evaporation of the resulting solution in vacuo gave a residue which was partitioned between ether (50 mL) and water (20 mL). After separating the phases, the aqueous phase was extracted with diethyl ether 50 mL. The diethyl ether extracts were combined, washed with aqueous $NaHCO_3$ and saturated brine, dried ($MgSO_4$) and evaporated in vacuo to provide a viscous oil which was chromatographed on silica gel (230 400 mesh, 3×15 cm). Elution with isopropanol-hexane (1:3; v:v) afforded the title compound as a colorless solid, mp 186°–187° C. after recrystallization from diethyl ether hexane; $1_H$ nmr ($CDCl_3$) δ 1.11 (6H, s), 2.88 (3H, s), 2.96 (3H, s), 4.37 (H, m), 4.54 (H, m), 5.17 (H, m).

Anal. Calc'd for $C_{27}H_{45}NO_6$: C, 67.61; H, 9.46; N, 2.92 Found: C, 67.26; H, 9.64; N, 2.77.

EXAMPLE 19

Preparation of 6(R)-[2-[8(S)-(2,2-Dimethylbutyryloxy)-2(S)-methyl-6(S)-aminocarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one (a) 6(R)-[2-[8(S)-(2,2-Dimethylbutyryloxy)-2(S)-methyl-6(S)-aminocarbonyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (19a)

By substituting an equimolar amount of ammonia for the dimethylamine used in Step (g) of Example 18 and using the procedure described therein, there was obtained the title compound as a colorless oil; $1_H$ nmr ($CDCl_3$) δ 0.073 (3H, s), 0.082 (3H, s), 0.883 (9H, s), 1.14 (6H, s), 4.28 (H, m), 4.56 (H, m), 5.08 (H, m), 5.28 (H, bs), 5.52 (H, bs).

(b) 6(R)-[2-[8(S)-(2,2-Dimethylbutyryloxy)-2(S)-methyl-6(S)-aminocarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one (19b)

By substituting an equimolar amount of compound 19a for compound 18g used in Step (h) of Example 18 and using the procedure described therein, there was obtained the title compound as a colorless solid, mp 116°–118° C.; $1_H$ nmr ($CDCl_3$) δ 0.82 (3H, d, J=7 Hz), 0.83 (3H, t, J=7 Hz), 1.14 (3H, s), 1.15 (3H, s), 4.36 (H, m), 4.56 (H, m), 5.10 (H, m), 5.22 (H, bs), 5.50 (H, bs).

Anal Calc'd for $C_{25}H_{41}NO_6$: C,66.49; H, 9.15; N, 3.10. Found: C,66.79; H, 9.35; N, 2.86.

EXAMPLE 20

Preparation of 6(R)-[2-[8(S)-(2,2-Dimethylbutyryloxy)-2(S)-methyl-6(S)-ethoxycarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one (a) 6(R)-[2-[8(S)-(2,2-Dimethylbutyryloxy)-2(S)-methyl-6(S)-ethoxycarbonyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (20a)

To a stirred solution of compound 18f (120 mg, 0.205 mmol) in pyridine (5 mL) was added 4-dimethylaminopyridine (25 mg, 0.205 mmol) and EtOH (33 mg, 0.72 mmol). The resulting mixture was stirred at ambient temperature for 4 days and then was partitioned between cold 3N HCl and ether. The organic phase was separated, washed with 3N HCl (until pH 4 was sustained in the aqueous phase), washed with aqueous $NaHCO_3$, dried ($Na_2SO_4$) and filtered. Evaporation of the filtrate in vacuo gave an oily resiue which was purified by flash chromatography on silica gel. Elution with $CH_2Cl_2$ acetone (95:5; v:v) afforded the title compound as a viscous oil; $1_H$ nmr ($CDCl_3$) δ 0.88 (9H, s), 1.08 (3H, s), 1.11 (3H, s), 2.14 (H, d, J=12 Hz), 2.5–2.7 (3H, m), 4.0 (H, m), 4.18 (H, m), 4.28 (H, m), 4.55 (H, m), 5.13 (H, m).

(b) 6(R)-[2-[8(S)-(2,2-Dimethylbutyryloxy)-2(S)-methyl-6(S)-ethoxycarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one (20b)

To a stirred solution of compound 20a (38 mg, 0.055 mmol) and acetic acid (26 ml) in THF (1 mL) was added tetra n butylammonium fluoride (1M in THF, 320 mL, 0.32 mmol). The resulting mixture was stirred at room temperature for 20 hours and then poured into cold aqueous $NaHCO_3$ and extracted with diethyl ether. The organic phase was separated, dried ($Na_2SO_4$), filtered and evaporated in vacuo to yield the title compound as a viscous oil; $1_H$ nmr ($CDCl_3$) δ 0.82 (3H, d, J=7 Hz), 0.83 (3H, t, J=7 Hz), 1.07 (3H, s), 1.11 (3H, s), 2.15 (H, d, J=12 Hz), 2.74 (H, d of d, J=16, 4 Hz), 4.03 (H, m), 4.18 (H, m), 4.37 (H, m), 4.57 (H, m), 5.19 (H, m).

Anal Calc'd for $C_{27}H_{44}O_7$: C, 67.47; H, 9.23. Found: C, 67.73; H, 9.43.

EXAMPLE 21

Preparation of 6(R)-[2-[8(S)-(2,2-Dimethylbutyryloxy)-2(S)-methyl-6(S)-isopropoxycarbonyl-1,2,3,4,4a(S),-5,6,7,8,8a(S)-decahydronaphthyl-1(S)]ethyl]-4(R)-hydroxy-3,4,5,6-tetrahydro-2H-pyran-2-one (a) 6(R)-[2-[8(S)-(2,2-Dimethylbutyryloxy)-2(S)-methyl-6(S)-isopropoxycarbonyl-1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (21a)

To a stirred solution of compound 18e (140 mg, 0.247 mmol), 4-dimethylaminopyridine (14 mg, 0.112 mmol) and isopropanol (39 mg, 0.67 mmol) in $CH_2Cl_2$ (300 μL) cooled to 0° C. was added dropwise a solution of N,N'-dicyclohexylcarbodiimide (76 mg, 0.37 mmol) in $CH_2Cl_2$ (500 μL). The resulting mixture was stirred and allowed to come to room temperature overnight. After collecting the precipitated solid, the filtrate was evaporated in vacuo to provide an oilY residue which was purified by flash chromatography on silica gel. Elution with $CH_2Cl_2$-acetone (98:2; v:v) afforded a mixture of the title compound [$1_H$ nmr $CDCl_3$) δ 0.88 (9H, s), 2.68 (2H, m), 4.28 (H, m), 4.55 (H, m), 4.95 (H, m), 5.13 (H, m)]and the acylurea by-product (19 by-product).

(b) 6(R)-[2-[8(S)-(2,2-Dimethylbutyryloxy)-2(S)-methyl-6(S)-isopropoxycarbonyl-1,2,3,4,4a(S),-5,6,7,8,8a(S)-decahydronaphthyl-1(S)]ethyl]-4(R)-hydroxy-3,4,5,6-tetrahydro-2H-pyran-2-one (19b)

To a stirred solution of the mixture (90 mg) of compounds 19a and 19 by-product and acetic acid (70 L) in THF (2.5 mL) was added tetra-n-butylammonium fluoride (1M in THF, 860 μL, 0.86 mmol). The resulting mixture was stirred at room temPerature for 20 hours and then poured into cold 5 aqueous $NaHCO_3$ and extracted with diethyl ether. The organic phase was separated, dried ($Na_2SO_4$), filtered and evaporated in vacuo to leave an oily residue which crystallized from diethyl ether-hexane to afford the title compound as a solid, mp 160°–161° C; $1_H$ nmr ($CDCl_3$) δ 0.82 (3H, d, J=7 Hz), 0.83 (3H, t, J=7 Hz), 1.10 (3H, s), 1.13 (3H, s), 1.20 (3H, d, J=6 Hz), 1.22 (3H, d, J=6 Hz), 2.15 (H, d, J=12 Hz), 2.74 (H, d of d, J=18, 6 Hz), 4.35 (H, 4.55 (H, m), 4.95 (H, m, 5.17 (H, m).

Anal Calc'd for $C_{28}H_{46}O_7$: C, 67.98; H, 9.37. Found: C, 68.08; H, 9.62.

EXAMPLE 22

Preparation of 6(R)-[2-[8(S)-(2,2-Dimethylbutyryloxy)-2(S)-methyl-6(S)-(N-cyclohexylaminocarbonyl,N-cyclohexyl) aminocarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one The title compound was isolated as the by product from Step (b) of Example 21 and was purified by recrystallization from diethyl ether hexane which afforded a solid, mp 137°–138° C.; $1_H$ nmr ($CDCl_3$) δ 1.08 (3H, s), 1.09 (3H, s), 2.60 (H, d of d, J=18, 5 Hz), 2.74 (H, d of d, J=18, 6 Hz), 2.88 (H, m), 3.63 (3H, m), 4.37 (H, m), 4.58 (H, m), 5.16 (H, m).

Anal. Calc'd for $C_{38}H_{62}N_2O_7$: C,69.26; H, 9.49;N, 4.25. Found: C,68.82; H, 9.70,N, 4.11.

EXAMPLE 23

Preparation of 6(R)-[2-[8(S)-(2,2-Dimethylbutyryloxy)-2(S)-methyl-6(R)-hydroxymethyl-1,2,3,4,4a(S),5,6,7,8,8 a(S)-decahydronaphthyl-1(S)]ethyl]-4(R)-hydroxy-3,4,5,6-tetrahydro-2H-pyran-2-one (a) 6(R)-[2-[8(S)-(2,2-Dimethylbutyryloxy)-2(S)-methyl-6(R)-formyl-1,2,3,4,4a(s),5,6,7,8,8a(s)-decahydronaphthyl-1(S)]ethyl]-4(R)-hydroxy-3,4,5,6-tetrahydro-2H-pyran-2-one (23a)

To a stirred solution of compound 18d (300 mg, 0 54 mmol) and acetic acid (0.35 mL) in THF (10 mL) was added tetra n butylammonium fluoride (1M in THF, 4.3 mL, 4.3 mmol. The resulting mixture was stirred at room temperature for 15 hours and then poured into cold water and extracted with diethyl ether. The organic phase was separated, washed with aqueous $NaHCO_3$, dried ($Na_2SO_4$, filtered and evaporated in vacuo to provide a residual oil which was purified by chromatography on silica gel. Elution with $CH_2Cl_2$ acetone (9:1; v:v) afforded an epimeric mixture of the title compound [$1_H$ nmr ($CDCl_3$) w 0.85 3H, d, J=7 Hz), 1.18 (3H, s), 5.28 H, m), 9.64 (H, d, J=1 Hz)]and the corresponding 6α-epimer [$1_H$ nmr ($CDCl_3$) δ 0.83 (3H, d, J=7 Hz), 1.10 (3H, s), 1.12 (3H, s), 5.24 (H, m), 9.60 (H, d, J=1 Hz)], 6(R)-[2-[8(S)-(2,2-dimethylbutyryloxy)-2(S)-methyl-6(S)-formyl-1,2,3,4,4a(S),5,6,7,8,8a(s) decahydronaphthyl-1(s)]ethyl]-4(R)-hydroxy-3,4,5,6-tetrahydro-2H-pyran-2-one (21 epimer). The mixture of epimers 23a and 23 epimer could be separated by chromatography or used as such in Step (b) below.

(b) 6(R)-[2-[8(S)-(2,2-Dimethylbutyryloxy)-2(S)-methyl-6(R)-hydroxymethyl-1,2,3,4,4a(S),5,6,7,8,8a(S)-decahydronaphthyl-1(S)]ethyl]-4(R)-hydroxy-3,4,5,6-tetrahydro-2H-pyran-2-one (23b)

By substituting an equimolar amount of the epimeric mixture of 23a and 23 epimer from Step (a) above for compound 2d in Step (e) of Example 2 and using the procedure described therein, there was obtained an epimeric mixture of the title compound and compound 2g, the latter being identical to an authentic sample of 2g prepared as described in Example 2. Separation of this epimeric mixture into pure compounds 23b and 2g could be accomplished by chromatography.

EXAMPLE 24

Preparation of 6(R)-[2-[8(S)-(2,2-Dimethylbutyryloxy)-2(S)-methyl-6(R)-carboxy-1,2,3,4,4a(S),5,6,7,8,8a(S)-decahydronaphthyl-1(S)] ethyl]-4(R)-hydroxy-3,4,5,6-tetrahydro-2H-pyran-2-one By substituting an equimolar amount of compound 23a for compound 7a in Step (b) of Example 7 and using the procedure described therein, there was obtained the title compound.

EXAMPLE 25

Preparation of 6(R)-[2-[8(S)-(2,2-Dimethylbutyryloxy)-2(S)-methyl-6(S)-phenylaminocarbonyloxymethyl-1,2,3,4,4a(S),5,6,7,8,8a(S)-decahydronaphthyl-1(S)]-ethyl]-4(R)-hydroxy-3,4,5,6-tetrahydro-2H-pyran-2-one By substituting an equimolar amount of compound 2h for the 6(R)-[2-[8(S)-(2,2-dimethylbutyryloxy)-2(S)-methyl-6(S)-hydroxymethyl-1,2,6,7,8,8a(R)-hexahydronaphthyl-1(S)]ethyl]-4(R)-hydroxy-3,4,5,6-tetrahydro-2H-pyran-2-one in Example 17 and using the procedure described therein, there was obtained the title compound.

EXAMPLES 28–35

Utilizing the general procedure described in Example 8 and starting with the 6-carboxy derivatives prepared according to the bioconversion reactions of Example 1, the following compounds of the formula (I) with the indicated absolute stereochemistry (AS) at C-6 are prepared from the appropriate diazoalkane:

| Compound Number | a | b | c | AS | R | $R^1$ |
|---|---|---|---|---|---|---|
| 28 | db | — | db | S | $CO_2Me$ | 1,1-dimethyl-propyl |
| 29 | db | — | db | R | $CO_2Me$ | 1,1-dimethyl-propyl |
| 30 | db | — | db | S | $CO_2iPr$ | sec-butyl |
| 31 | db | — | db | R | $CO_2iPr$ | sec-butyl |

Similarly, starting with the 6-carboxy derivatives which are prepared utilizing the general procedures of Examples 7 and 24, the following compounds of formula (I) with the indicated absolute stereochemistry (AS) at C-6 are also prepared:

| Compound Number | a | b | c | AS | R | $R^1$ |
|---|---|---|---|---|---|---|
| 32 | — | — | — | R | $CO_2iPr$ | 1,1-dimethyl-propyl |
| 33 | db | — | — | S | $CO_2Me$ | 1,1-dimethyl-propyl |
| 34 | — | db | — | S | $CO_2Me$ | 1,1-dimethyl-propyl |
| 35 | — | — | db | R | $CO_2Me$ | sec-butyl |

EXAMPLES 36–42

The following compounds of the formula (I) with the indicated absolute sterochemistry (AS) at C-6 and wherein R is $$CH_2OC(=O)R^5$$

are prepared from the corresponding compounds wherein R is $CH_2OH$ and in which the 4-hydroxy function of the lactone moiety is protected as a tetrahydropyranyl ether group by a standard acylation reaction utilizing the appropriate acyl halide or anhydride followed by the deprotection of the 4-hydroxy function:

| Compound Number | a | b | c | AS | R | $R^1$ |
|---|---|---|---|---|---|---|
| 36 | db | — | db | S | $CH_3CH_2C(=O)OCH_2$ | sec-butyl |
| 37 | db | — | db | S | $CH_3C(=O)OCH_2$ | 1,1-dimethylpropyl |
| 38 | — | — | — | S | $(CH_3)_2CHC(=O)OCH_2$ | sec-butyl |
| 39 | — | — | — | S | $CH_3CH_2C(CH_3)_2C(=O)OCH_2$ | 1,1-dimethylpropyl |
| 40 | db | — | — | R | $CH_3C(=O)OCH_2$ | 1,1-dimethylpropyl |
| 41 | — | db | — | S | $CH_3C(=O)OCH_2$ | 1,1-dimethylpropyl |
| 42 | — | — | db | S | $CH_3CH_2C(=O)OCH_2$ | sec-butyl |

EXAMPLES 43–49

Using the general procedure described in Example 17 and starting with the corresponding compounds wherein R is $CH_2OH$, the following compounds of the formula (I) with the indicated absolute stereochemistry (AS) at C-6, and wherein R is $$CH_2OC(=O)R^5$$

and $R^5$ is $NH_2$ or a substituted amino moiety, are prepared:

| Compound Number | a | b | c | AS | R | $R^1$ |
|---|---|---|---|---|---|---|
| 43 | db | — | db | R | $PhNHC(=O)OCH_2$ | 1,1-methylpropyl |
| 44 | db | — | db | S | $PhNHC(=O)OCH_2$ | sec-butyl |
| 45 | db | — | — | R | $PhNHC(=O)OCH_2$ | 1,1-dimethylpropyl |
| 46 | — | db | — | S | $PhNHC(=O)OCH_2$ | 1,1-dimethylpropyl |
| 47 | — | — | db | S | p-$FPhNHC(=O)OCH_2$ | sec-butyl |
| 48 | — | — | — | S | o-$FPhNHC(=O)OCH_2$ | 1,1-dimethylpropyl |
| 49 | — | — | — | R | $PhNHC(=O)OCH_2$ | sec-butyl |

EXAMPLES 50–57

Utilizing the general acylation procedures disclosed in co-pending patent applications Ser. No. 859,524, 859,534, 859,535, all filed May 5, 1986, the following compounds of the formula (I) with the indicated absolute stereochemistry (AS) at C-6 wherein the $R^1$ substituent is elaborated are prepared from the 6-carboxy, 6-alkoxycarbonyl, the protected 6-hydroxymethyl and the 6-acyloxymethyl derivatives.

| Compound Number | a | b | c | AS | R | $R^1$ |
|---|---|---|---|---|---|---|
| 50 | db | — | db | S | $CH_2OH$ | cyclohexyl- |
| 51 | db | — | db | R | $CH_2OH$ | $HOCH_2$ |
| 52 | db | — | db | S | $CO_2H$ | $CH_3COCH_2$ |
| 53 | — | — | — | S | $CO_2H$ | cyclobutyl- |
| 54 | — | — | — | R | $CH_2OH$ | $HOCH_2CH_2C(CH_3)_2$ |
| 55 | db | — | — | R | $CH_2OH$ | $HO(CH_2)_3C(CH_3)_2$ |
| 56 | — | db | — | S | $CO_2CH_3$ | $CH_3COCH_2CH_2C(CH_3)_2$ |
| 57 | — | — | db | S | $CO_2CH_2$—<br>\|<br>cyclohexyl | cyclohexyl |

EXAMPLE 58–62

Utilizing the methodology of Example 3 and the procedures disclosed in copending patent applications Ser. No. 131695 filed Dec. 12, 1987 and Ser. Nos. 161530, 161529 all filed Feb. 29, 1988 and the hydrogenation procedure in U.S. Pat. No. 4,444,784 the following compounds of the formula (I) with the indicated stereochemistry (AS) at C-6 are prepared.

| Compound Number | a | b | c | AS | R | $R^1$ |
|---|---|---|---|---|---|---|
| 58 | db | — | db | S | $CH_3CHOH$ | 1,1-methylpropyl |
| 59 | db | — | db | R | $CH_3CHOH$ | 1,1-methylpropyl |
| 60 | db | — | db | S | $CH_3CHOH$ | sec-butyl |
| 61 | db | — | db | R | $CH_3CHOH$ | sec-butyl |
| 62 | db | — | — | R | $CH_3CHOH$ | 1,1-methylpropyl |

EXAMPLE 63

Preparation of Ammonium Salts of Compounds II

The lactone 2h (1.0 mmol) from Example 2 is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried ($MgSO_4$). The $MgSO_4$ is removed by filtration and the filtrate saturated with ammonia (gas to give a gum which solidified to provide the ammonium salt.

EXAMPLE 64

Preparation of Alkali and Alkaline Earth Salts of Compounds II

To a solution of 42 mg of lactone 2h from Example 2 in 2 ml of ethanol is added 1 ml of aqueous NaOH (1 equivalent). After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 65

Preparation of Ethylenediamine Salts of Compounds II

To a solution of 0.50 g of the ammonium salt from Example 63 in 10 ml of methanol is added 75 ml of ethylenediamine. The methanol is stripped off under vacuum to obtain the desired ethylenediamine salt.

EXAMPLE 66

Preparation of Tris(hydroxymethyl)aminomethane Salts of Compounds II

To a solution of 202 mg of the ammonium salt from Example 63 in 5 ml of methanol is added a solution of 60.5 mg of tris(hydroxymethyl) aminomethane in 5 ml of methanol. The solvent is removed in vacuo to afford the desired tris(hydroxy methyl)aminomethane salt.

EXAMPLE 67

Preparation of L-Lysine Salts of Compounds II

A solution of 0 001 mole of L-lysine and 0.0011 mole of the ammonium salt from Example 63 in ml of 85% ethanol is concentrated to dryness in vacuo to give the desired L-lysine salt.

Similarly prepared are the L-arginine, L-ornithine, and N-methylglucamine salts.

EXAMPLE 68

Preparation of Tetramethylammonium Salts of Compounds II

A mixture of 68 mg of ammonium salt from Example 63 in 2 ml of methylene chloride and 0.08 ml of 24% tetramethylammonium hydroxide in methanol is diluted with ether to yield the desired tetramethylammonium salt.

EXAMPLE 69

Preparation of Methyl Esters of Compounds II

To a solution of 400 mg of lactone 2h from Example 2 in 100 ml of absolute methanol is added 10 ml 0.1 M sodium methoxide in absolute methanol. This solution is allowed to stand at room temperature for one hour, then is diluted with water and extracted twice with ethyl acetate. The organic phase is separated, dried ($Na_2SO_4$), filtered and evaporated in vacuo to yield the desired methyl ester.

In like manner, by the use of equivalent amounts of propanol, butanol, isobutanol, t-butanol, amylalcohol, isoamylalcohol, 2-dimethylaminoethanol, benzylalcohol, phenethanol, 2-acetamidoethanol and the like, and employing the corresponding alcohol as solvent, the corresponding esters are obtained.

EXAMPLE 70

Preparation of Free Dihydroxy Acids

The sodium salt of the compound II from Example 64 is dissolved in 2 ml of ethanol-water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative derived slowly reverts to the corresponding, parent lactone on standing. The dihydroxy acid can be maintained by increasing the pH above 7.0.

EXAMPLE 71

As a specific embodiment of a composition of this invention, 20 mg of lactone 2h from Example 2, is formulated with sufficient finely divided lactose to provide a total amount of 580 to 590 mg to fill a size 0, hard gelatin capsule.

What is claimed is:

1. A compound represented by the following structural formula (I):

(I)

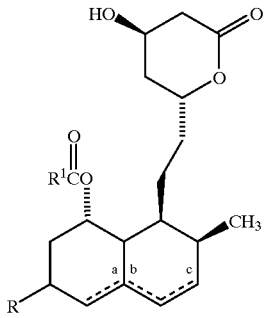

wherein:

R is

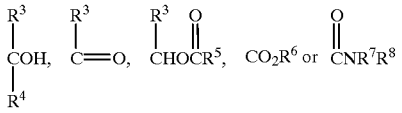

$R^1$ and $R^5$ are independently:

(1) $C_{1-10}$ alkyl;

(2) substituted $C_{1-10}$ alkyl in which one or more substituent(s) is:

(a) halogen, (b) hydroxy, (c) $C_{1-10}$ alkoxy, (d) $C_{1-5}$ alkoxycarbonyl, (e) $C_{1-5}$ acyloxy, (f) $C_{3-8}$ cycloalkyl, (g) phenyl, (h) substituted phenyl in which the substituents are X and Y, (i) $C_{1-10}$ alkyl$S(O)_n$ in which n is 0 to 2, (j) $C_{3-8}$ cycloalkyl$S(O)_n$, (k) phenyl$S(O)_n$, (l) substituted phenyl$S(O)_n$ in which the substituents are X and Y, and (m) oxo;

(3) $C_{1-10}$ alkoxy;

(4) $C_{2-10}$ alkenyl;

(5) $C_{3-8}$ cycloalkyl;

(6) substituted $C_{3-8}$ cycloalkyl in which one substituent is:

(a) $C_{1-10}$ alkyl (b) substituted $C_{1-10}$ alkyl in which the substituent is selected from (i) halogen, (ii) hydroxy, (iii) $C_{1-10}$ alkoxy, (iv) $C_{1-5}$ alkoxycarbonyl, (v) $C_{1-5}$ acyloxy, (vi) phenyl, (vii) substituted phenyl in which the substituents are X and Y (viii) $C_{1-10}$ alkyl$S(O)_n$, (ix) $C_{3-8}$ cycloalkyl$S(O)_n$, (x) phenyl$S(O)_n$, (xi) substituted phenyl$S(O)_n$ in which the substituents are X and Y, and (xii) oxo, (c) $C_{1-10}$ alkyl$S(O)_n$, (d) $C_{3-8}$ cycloalkyl$S(O)_n$, (e) phenylS(O)$_n$,
(f) substituted phenylS(O)$_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y; and $R^9S$ in which $R^9$ is selected from
(a) $C_{1-10}$ alkyl,
(b) phenyl, and
(c) substituted phenyl in which the substituents are X and Y;

$R^6$ are independently:
(1) hydrogen;
(2) $C_{1-5}$ alkyl;
(3) substituted $C_{1-5}$ alkyl in which the substituent is:
(a) phenyl,
(b) dimethylamino, and
(c) acetylamino, and
(4) 2,3-dihydroxypropyl;

$R^3$ and $R^4$ are independently:
(1) hydrogen;
(2) $C_{1-10}$ alkyl;
(3) substituted $C_{1-10}$ alkyl in which one or more substituent(s) is:
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkylS(O)$_n$,
(j) $C_{3-8}$ cycloalkylS(O)$_n$,
(k) phenylS(O)$_n$,
(l) substituted phenylS(O)$_n$ in which the substituents are X and Y, and
(m) oxo;
(4) $C_{2-10}$ alkenyl;
(5) substituted $C_{2-10}$ alkenyl in which one or more substituent(s) is:
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkylS(O)$_n$,
(j) $C_{3-8}$ cycloalkylS(O)$_n$,
(k) phenylS(O)$_n$,
(l) substituted phenylS(O)$_n$ in which the substituents are X and Y, and
(m) oxo;
(6) $C_{3-8}$ cycloalkyl;
(7) substituted $C_{3-8}$ cycloalkyl in which one substituent is:
(a) $C_{1-10}$ alkyl
(b) substituted $C_{1-10}$ alkyl in which the substituent is
(i) halogen,
(ii) hydroxy,
(iii) $C_{1-10}$ alkoxy,
(iv) $C_{1-5}$ alkoxycarbonyl,
(v) $C_{1-5}$ acyloxy
(vi) phenyl,
(vii) substituted phenyl in which the substituents are X and Y
(viii) $C_{1-10}$ alkylS(O)$_n$,
(ix) $C_{3-8}$ cycloalkylS(O)$_n$,
(x) phenylS(O)$_n$ in which the substituents are X and Y, and
(xii) oxo,
(c) $C_{1-10}$ alkylS(O)$_n$,
(d) $C_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;
(8) phenyl;
(9) substituted phenyl in which the substituents are X and Y;

$R^7$ and $R^8$ are independently:
(1) hydrogen;
(2) $C_{1-10}$ alkyl;
(3) substituted $C_{1-10}$ alkyl in which one or more substituent(s) is:
(a) halogen,
(b) hydroxy,
(c) $C_{1-10}$ alkoxy,
(d) $C_{1-10}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkyl S(O)$_n$ in which n is 0 to 2,
(j) $C_{3-8}$ cycloalkyl S(O)$_n$,
(k) phenyl S(O)$_n$;
(l) substituted phenyl S(O)$_n$ in which the substituents are X and Y, and
(m) oxo;
(4) $C_{2-10}$ alkenyl;
(5) $C_{3-8}$ cycloalkyl;
(6) aminocarbonyl;
(7) substituted aminocarbonyl in which one or more substituent(s) is:
(a) $C_{1-5}$ alkyl,
(b) $C_{3-8}$ cycloalkyl, (c) phenyl,
(d) substituted phenyl in which the substituents are X and Y;
(8) phenyl;
(9) substituted phenyl in which the substituents are X and Y;
(10) $C_{1-10}$ alkylcarbonyl;
(11) $C_{3-8}$ cycloalkylcarbonyl;
(12) phenylcarbonyl;
(13) substituted phenylcarbonyl in which the substituents are X and Y; and X and Y independently are hydrogen, halogen, trifluoromethyl, $C_{1-3}$ alkyl, nitro, cyano or a group selected from:

(1) $R^{10}O\ (CH_2)_m$ in which m is 0 to 3 and $R^{10}$ is hydrogen, $C_{2-3}$alkyl or hydroxy $C_{2-3}$alkyl;
(2)

$$R^{11}\overset{\overset{\displaystyle O}{\|}}{C}O(CH_2)_m \quad \text{or} \quad R^{11}O\overset{\overset{\displaystyle O}{\|}}{C}O(CH_2)_m$$

in which $R^{11}$ is hydrogen, $C_{1-3}$alkyl, hydroxy-$C_{2-3}$alkyl, phenyl, naphthyl, amino $C_{1-3}$alkyl, $C_{1-3}$alkylamino-$C_{1-3}$alkyl, di($C_{1-3}$alkyl)amino-$C_{1-3}$alkyl, hydroxy $C_{2-3}$alkylamino-$C_{1-3}$alkyl or di(hydroxy $C_{2-3}$alkyl) amino $C_{1-3}$alkyl;
(3)

$$R^{12}O\overset{\overset{\displaystyle O}{\|}}{C}(CH_2)_m$$

in which $R^{12}$ is hydrogen, $C_{1-3}$alkyl, hydroxy-$C_{2-3}$alkyl, $C_{1-3}$alkoxy-$C_{1-3}$alkyl, phenyl or naphthyl;
(4)

$$R^{13}R^{14}N(CH_2)_m, \quad R^{13}R^{14}N\overset{\overset{\displaystyle O}{\|}}{C}(CH_2)_m \quad \text{or} \quad R^{13}R^{14}N\overset{\overset{\displaystyle O}{\|}}{C}O(CH_2)_m$$

in which $R^{13}$ and $R^{14}$ independently are hydrogen, $C_{1-3}$ alkyl, and hydroxy-$C_{2-3}$alkyl;
(5) $R^{15}S(O)_n(CH_2)m$ in which $R^{15}$ is hydrogen, $C_{1-3}$alkyl, amino, $C_{1-3}$alkylamino or di($C_{1-3}$alkyl)amino; and a, b and c each represent single bonds or one of a, b and c represents a double bond or both a and c represent double bonds; or a pharmaceutically acceptable salt thereof.

2. A compound of claim 1 wherein:

$R^1$ and $R^5$ are independently:
(1) $C_{1-10}$ alkyl;
(2) substituted $C_{1-10}$ alkyl in which one or more substituent(s) is:
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y, and
(i) oxo;
(3) $C_{3-8}$ cycloalkyl;
(4) substituted $C_{3-8}$ cycloalkyl in which one substituent is:
(a) $C_{1-10}$ alkyl,
(b) substituted $C_{1-10}$ alkyl in which the substituent is
(i) halogen,
(ii) hydroxy,
(iii) $C_{1-10}$ alkoxy
(iv) $C_{1-5}$ acyloxy,
(v) $C_{1-5}$ alkoxycarbonyl,
(vi) phenyl,
(vii) substituted phenyl in which the substituents are X and Y, and
(viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

3. A compound of claim 2 wherein:

$R^1$ and $R^5$ are independently:
(1) $C_{1-10}$ alkyl;
(2) $C_{3-8}$ cycloalkyl;
(3) phenylamino; and
(4) substituted phenylamino in which the substituents are X and Y.

4. A compound of claim 3 wherein:

$R^3$ and $R^4$ are independently:
(1) hydrogen;
(2) $C_{1-10}$ alkyl;
(3) $C_{3-8}$ cycloalkyl; and
(4) phenyl.

5. A compound of claim 4 wherein:

$R^7$ and $R^8$ are independently:
(1) hydrogen;
(2) $C_{1-10}$ alkyl;
(3) $C_{3-8}$ cycloalkyl;
(4) aminocarbonyl;
(5) substituted aminocarbonyl in which one or more substituent(s) is:
(a) $C_{1-5}$ alkyl,
(b) $C_{3-8}$ cycloalkyl,
(c) phenyl,
(d) substituted phenyl in which the substituents are X and Y.

6. A compound of claim 5 wherein $R^1$ is 1,1-dimethylpropyl or sec-butyl.

7. A compound of claim 6 wherein $R^3$ and $R^4$ are independently selected from:
(1) hydrogen;
(2) $C_{1-5}$ alkyl; and
(3) phenyl.

8. A compound of claim 7 wherein a and c represent double bonds.

9. A compound of claim 8 wherein R is

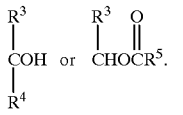

10. A compound of claim 9 selected from the group consisting of:

[(1) 6(R)-[2-[8(S)-(2,2-dimethylbutyryloxy)-2(S)-methyl-6(S)-hydroxymethyl-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-(2-methylbutyryloxy)-(S)-methyl-6(S)-hydroxymethyl-1,2,6,7,8,8a(R)-hexahydronaphthyl-1(S)]ethyl]-4(R)-hydroxy-3,4,5,6-tetrahydro-2H-pyran-2-one;

(3)] *(1)* 6(R)-[2-[8(S)-(2,2-dimethylbutyryloxy)-2(S)-methyl-6(R)-hydroxymethyl-1,2,6,7,8,8a-(R)-hexahydronaphthyl-1(S)]ethyl]-4(R)-hydroxy-3,4,5,6-tetrahydro-2H-pyran-2-one; *and*

*(2) 6(R)-[2-[8(S)-(2,2-dimethylbutyryloxy)-6(S)-phenylaminocarbonyloxymethyl-2(S)-methyl-1,2,6,7,8,8a(R)-hexahydronaphthyl-1(S)]ethyl]-4(R)-hydroxy-3,4,5,6-tetrahydro-2H-pyran-2-one*

[(4) 6(R)-[2-[B(S)-(2,2-dimethylbutyryloxy)-(S)-methyl-6(S)--phenylaminocarbonyloxymethyl-1,2,6,7,8,8a(R)-hexahydronaphthyl-1(S)]ethyl]-4(R)-hydroxy-3,4,5,6-tetrahydro-2H-pyran-2-one].

11. A compound of claim 8 wherein R is $CO_2R^6$ or

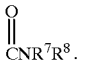

12. A compound of claim 11 selected from the group consisting of:

[(1) 6(R)-[2-[8(S)-(2,2-dimethylbutyryloxy)-(S)-methyl-6(S)-carboxy-1,2,6,7,8,8a(R)-hexahydro-naphthyl-1(S)]ethyl]-4(R)-hydroxy-3,4,5,6-tetrahydro-H-pyran-2-one;

(2) 6(R)-[2-[8(S)-(2-methylbutyryloxy)-2(S)-methyl-6(S)-carboxy-1,2,6,7,8,8a(R)-hexahydronaphthyl-(S)]ethyl]-4(R)-hydroxy-3,4,5,6-tetrahydro-H-pyran-2-one;

(3)] *(1)* 6(R)-[2-[8(S)-(2,2-dimethylbutyryloxy)-2(S)-methyl-6(R)-carboxy-1,2,6,7,8,8a(R)-hexahydronaphthyl-1(S)]ethyl]-4(R)-hydroxy-3,4,5,6-tetrahydro-2H-pyran-2-one;

[(4)] *(2)* 6(R)-[2-[8(S)-(2,2-dimethylbutyryloxy)-2(S)-methyl-6(S)-(N,N-dimethyl)aminocarbonyl-1,2,6,7,8,8a(R)-hexahydronaphthyl-1(S)]ethyl]-4(R)-hydroxy-3,4,5,6-tetrahydro-2H-pyran-2-one;

[(5)] *(3)* 6(R)-[2-(8(S)-(2,2-dimethylbutyryloxy)-2(S)-methyl-6(R)-aminocarbonyl-1,2,6,7,8,8a(R)-hexahydronaphthyl-1(S)]ethyl]-4(R)-hydroxy-3,4,5,6-tetrahydro-2H-pyran-2-one; *and*

[(6)] *(4)* 6(R)-[2-(8(S)-(2-methylbutyryloxy)-2(S)-methyl-6(S)-aminocarbonyl-1,2,6,7,8,8a(R)-hexahydronaphthyl-1(S)]ethyl]-4(R)-hydroxy-3,4,5,6-tetrahydro-2H-pyran-2-one[; and the corresponding dihydroxy acids, and esters thereof].

13. A compound of claim 9 selected from the group consisting of:

(1) 6(R)-[2-[8(S)-(2,2-dimethylbutyryloxy)-2(S)-methyl-6(S)-(1-hydroxyethyl) 1,2,6,7,8,8a-(R)-hexahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-(1-hydroxyethyl) 1,2,6,7,8,8a(R)-hexahydronaphthyl-1(S)]ethyl]-4(R)-hydroxy-3,4,5,6-tetrahydro-2H-pyran-2-one;

(3) 6(R)-[2-[8(S)-(2 -methylbutyryloxy)-2(S)-methyl-6(S)-(1-hydroxyethyl) 1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-(2-methylbutyryloxy)-2(S)-methyl-6(R)-(1-hydroxyethyl)-1,2,6,7,8,8a(R)-hexahydronaphthyl-1(S)]ethyl,]4(R)-hydroxy-3,4,5,6-tetrahydro-2H-pyran-2-one.

14. A compound of claim 7 wherein a, b and c represent single bonds.

15. A compound of claim 14 wherein R is

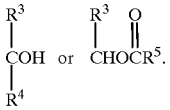

16. A compound of claim 15 selected from the group consisting of:

(1) 6(R)-[2-[8(S)-(2,2-dimethylbutyryloxy)-2(S)-methyl-6(S)-hydroxymethyl-1,2,3,4,4a(S),5,6,7,8,8a(S)-decahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(S)-(2,2-dimethylbutyryloxymethyl)-1,2,3,4,4a(S),5,6,7,8,8a(S)-decahydronaphthyl-1(S)]-ethyl]-4(R)-hydroxy-3,4,5,6-tetrahydro-2H-pyran-2-one;

(3) 6(R)-[2-[8(S)-(2,2-dimethylbutyryloxy)-2(S)-methyl-6(R)-(1-hydroxyethyl)-1,2,3,4,4a(S),5,6,7,8,8a(S)-decahydronaphthyl-1(S)]ethyl]-4(R)-hydroxy-3,4,5,6-tetrahydro-2H-pyran-2-one;

(4) 6(R)-[2-[8(S)-(2,2-dimethylbutyryloxy)-2(S)-methyl-6(S)-(1-hydroxyethyl) 1,2,3,4,4a(S),5,6,7,8,8a(S)-decahydronaphthyl-1(S)]ethyl]-4(R)-hydroxy-3,4,5,6-tetrahydro-2H-pyran-2-one;

(5) [6(R)-[2 (8(S)-(2,2-dimethylbutyryloxy)-2(S)-methyl-6(S)-(1-hydroxyphenylmethyl)-1,2,3,4,4a-(S),5,6,7,8,8a(S)-decahydronaphthyl-1(S)]ethyl]-4(R)-hydroxy-3,4,5,6-tetrahydro-2H-pyran-2-one]*6(R)-[2-[8(S)-(2,2-dimethylbutyryloxy)-2(S)-methyl-6(S)-(1-hydroxyphenylmethyl-1,2,3,4,4a(S),5,6,7,8,8a(S)-decahydronaphthyl-1(S)]ethyl]-4(R)-hydroxy-3,4,5,6-tetrahydro-2H-pyran-2-one.*

17. A compound of claim 14 wherein R is

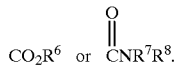

18. A compound of claim 17 selected from the group consisting of:

(1) 6(R)-[2-[8(S)-(2,2-dimethylbutyryloxy)-2(S)-methyl-6(S)-carboxy-1,2,3,4,4a(S),5,6,7,8,8a(S)-decahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(S)-ethoxycarbonyl-1,2,3,4,4a(S),5,6,7,8,8a(S)- decahydronaphthyl-1(S)]ethyl]-4(R)-hydroxy-3,4,5,6-tetrahydro-2H-pyran-2-one;

(3) 6(R)-[2-[8(S)-(2,2-dimethylbutyryloxy)-2(S)-methyl-6(S)-aminocarbonyl-1,2,3,4,4a(S),5,6,7,8,8a(S)-decahydronaphthyl-(S)]ethyl]-4(R)-hydroxy-3,4,5,6-tetrahydro-2H-pyran-2-one; *and*

(4) 6(R)-[2-[8(S)-(2,2-dimethylbutyryloxy)-2(S)-methyl-6(S)-(N-cyclohexylaminocarbonyl,N-cyclohexyl) aminocarbonyl-1,2,3,4,4a(S),5,6,7,8,8a(S)-decahydronaphthyl-1(S)]ethyl]-4(R)-hydroxy-3,4,5,6-tetrahydro-2H-pyran-2-one[; and the corresponding ring opened dihydroxy acids, and esters thereof].

19. A compound of claim 14 wherein R is

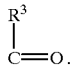

20. A compound of claim 19 which is:

[6(R)-[2 (8(S)-(2,2-dimethylbutyryloxy)-2(S)-methyl-6 (S)-(1 oxoethyl) 1,2,3,4,4a(S),5,6,7,8,a(S)-decahydronaphthyl-1(S)]ethyl]-4(R)-hydroxy-3,4,5,6-tetrahydro-2H-pyran-2-one and the corresponding ring opened dihydroxy acid, and esters thereof] *6(R)-[2-[8(S)-(2,2-dimethylbutyryloxy)-2(S)-methyl-6(S)-(1-oxoethyl)-1,2,3,4,4a(S),5,6,7,8,8a(S)-decahydronaphthyl-1(S)]ethyl]-4(R)-hydroxy-3,4,5,6-tetrahydro-2H-pyran-2-one.*

21. A compound of claim 7 wherein one of a, b and c represents a double bond.

22. A compound of claim 21 wherein R is

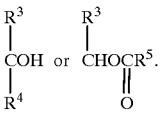

23. A compound of claim 22 selected from the group consisting of:

(1) 6(R)-[2-[8(S)-(2,2-dimethylbutyryloxy)-2(S)-methyl-6(R)-hydroxymethyl-1,2,3,4,6,7,8,8a-(R)-octahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-(2,2-dimethylbutyryloxymethyl)-1,2,3,4,6,7,8,8a (R)-octahydronaphthyl-(S)]ethyl]-4(R)-hydroxy-3,4,5, 6-tetrahydro-2H-pyran-2-one;

(3) 6(R)-[2-[8(S)-(2,2-dimethylbutyryloxy)-2(S)-methyl-6(R)-(1 hydroxyethyl) 1.2.3,4,6,7,8,8a(R)-octahydronaphthyl-1(S)]ethyl]-4(R)-hydroxy3,4,5,6-tetrahydro-2H-pyran-2-one.

24. A hypocholesterolemic, hypolipidemic pharmaceutical composition comprising a pharmaceutically acceptable carrier and a nontoxic effective amount of a compound as defined in claim 1.

25. A method of inhibiting cholesterol biosynthesis comprising the administration to a subject in need of such treatment a nontoxic therapeutically effective amount of a compound of claim 1.

*26. The compound of claim 9 which is 6(R)-[2-[8(S)-(2,2-dimethylbutyryloxy)-2(S)-methyl-6(S)-hydroxymethyl-1,2,3,4,4a(R)-hexahydronaphthyl-1(S)]ethyl]-4(R)-hydroxy-3,4,5,6-tetrahydro-2H-pyran-2-one.*

*27. The compound of claim 9 which is 6(R)-[2-[8(S)-(2-methylbutyryloxy)-2(S)-methyl-6(S)-hydroxymethyl-1,2,6,7,8,8a(R)-hexahydronaphthyl-1(S)]ethyl]-4(R)-hydroxy-3,4,5,6-tetrahydro-2H-pyran-2-one.*

*28. The compound of claim 11 which is 6(R)-[2-[8(S)-(2,2-dimethylbutyryloxy)-2(S)-methyl-6(S)-carboxy-1,2,6,7,8,8a(R)-hexahydronaphthyl-1(S)]ethyl]-4(R)-hydroxy-3,4,5,6-tetrahydro-2H-pyran-2-one.*

*29. The compound of claim 11 which is 6(R)-[2-[8(S)-(2-methylbutyryloxy)-2(S)-methyl-6(S)-carboxy--1,2,6,7,8,8a (R)-hexahydronaphthyl-1(S)]ethyl]-4(R)-hydroxy-3,4,5,6-tetrahydro-2H-pyran-2-one.*

* * * * *